US009871270B2

(12) United States Patent
Hariprakasha et al.

(10) Patent No.: US 9,871,270 B2
(45) Date of Patent: Jan. 16, 2018

(54) FUNCTIONALIZED IONIC LIQUIDS AND THEIR APPLICATIONS

(71) Applicant: Materials Modification Inc, Fairfax, VA (US)

(72) Inventors: Humcha Krishnamurthy Hariprakasha, Frederick, MD (US); Krishnaswamy Kasthuri Rangan, Fairfax, VA (US); Tirumalai Srinivas Sudarshan, Vienna, VA (US)

(73) Assignee: MATERIALS MODIFICATION, INC., Fairfax, VA (US)

( * ) Notice: Subject to any disclaimer, the term of this patent is extended or adjusted under 35 U.S.C. 154(b) by 0 days.

(21) Appl. No.: 15/444,192

(22) Filed: Feb. 27, 2017

(65) Prior Publication Data
US 2017/0170518 A1 Jun. 15, 2017

Related U.S. Application Data

(62) Division of application No. 14/213,428, filed on Mar. 14, 2014.

(60) Provisional application No. 61/787,788, filed on Mar. 15, 2013.

(51) Int. Cl.
*H01M 10/0567* (2010.01)
*D06M 13/473* (2006.01)
*H01M 10/42* (2006.01)
*H01M 10/0566* (2010.01)
*H01M 12/02* (2006.01)
*H01M 12/08* (2006.01)
(Continued)

(52) U.S. Cl.
CPC ...... *H01M 10/0567* (2013.01); *C07D 233/61* (2013.01); *D06M 13/473* (2013.01); *H01M 10/0525* (2013.01); *H01M 10/0566* (2013.01); *H01M 10/4235* (2013.01); *H01M 12/02* (2013.01); *H01M 12/08* (2013.01); *D06M 2200/30* (2013.01); *H01M 2300/0025* (2013.01)

(58) Field of Classification Search
CPC ........ H01M 10/0567; H01M 10/0525; H01M 10/0566; H01M 12/02; H01M 12/08; H01M 10/4235; H01M 2300/0025; C07D 233/61; D06M 13/473; D06M 2200/30
See application file for complete search history.

(56) References Cited

U.S. PATENT DOCUMENTS

| 4,750,911 A | 6/1988 | Hansen |
| 6,045,719 A | 4/2000 | Meszaros et al. |
| 6,660,046 B1 | 12/2003 | Terranova et al. |

(Continued)

FOREIGN PATENT DOCUMENTS

| EP | 1820537 A1 | 8/2002 |
| EP | 1820537 A1 | 8/2007 |

OTHER PUBLICATIONS

Blanchard LA, Gu Z and Brenncke JF, High-Pressure Phase Behavior of Ionic Liquid/CO2 systems, J. Phys. Chem. B, 105:2437-2444 (2001), American Chemical Society.

(Continued)

*Primary Examiner* — Rosalynd A Keys
(74) *Attorney, Agent, or Firm* — Jyoti C Iyer

(57) ABSTRACT

Disclosure of functionalized ionic liquids. Use of disclosed ionic liquids as solvent for carbon dioxide. Use of disclosed ionic liquids as flame retardant. Use of disclosed ionic liquids for coating fabric to obtain flame retardant fabric.

8 Claims, 22 Drawing Sheets

(51) Int. Cl.
   *C07D 233/61* (2006.01)
   *H01M 10/0525* (2010.01)

(56) References Cited

U.S. PATENT DOCUMENTS

2011/0073331 A1* 3/2011 Xu .................. C07F 9/5407
                                                    169/46
2011/0319633 A1   12/2011 Shiflett et al.

OTHER PUBLICATIONS

Baltus RE, Culbertson BH, Dai S, Luo H, and DePaoli DW, J. Phys. Chem. B, 108:721-727(2004), American Chemical Society.
Muldoon MJ, Aki SNVK, Anderson JL, Dixon JK, and Brennecke JF, Improving Carbon Dioxide Solubility in Ionic Liquids, J. Phys. Chem., 111:9001-9009 (2007).
Puxty G, Rowland R, Allport A, Yang Q, Bown M, Burns R, Maeder M, and Attalla M, Environ. Sci. Technol., 43:6427-6433 (2009), American Chemical Society.
Goodrich BF, de la Fuente JC, Gurkan BE, Zadigian DJ, Price EA, Huang Y, and Brennecke JF, Environ. Sci. Technol., 43:6427-6433 (2009), American Chemical Society.

Ten (10) pages of International Search Report and Written Opinion dated Oct. 7, 2014, issued in International Appl. Ser. No. PCT/US/2014/028973 filed Mar. 14, 2014.
Ten (10) pages of European Supplementary Search dated Jan. 31, 2017.
Baltus RE, Culbertson BH, Dai S, Luo H, and DePaoli DW, Low-Pressure Solubility of Carbon Dioxide in Room-Temperature Ionic Liquids Measured with a Quartz Crystal Microbalance, J. Phys. Chem. B, 108:721-727 (2004), American Chemical Society.
Muldoon MJ, Aki SNVK, Anderson JL, Dixon JK, and Brennecke JF, Improving Carbon Dioxide Solubility in Ionic Liquids, J. Phys. Chem., 111:9001-9009 (2007), American Chemical Society.
Puxty G, Rowland R, Allport A, Yang Q, Bown M, Burns R, Maeder M, and Attalla M, Carbon Dioxide Postcombustion Capture: A Novel Screening Study of the Carbon Dioxide Absorption Performance of 76 Amines, Environ. Sci. Technol., 43:6427-6433 (2009), American Chemical Society.
Goodrich BF, de la Fuente JC, Gurkan BE, Zadigian DJ, Price EA, Huang Y, and Brennecke JF, Experimental Measurements of of Amine -Functionalized Anion-Tethered Ionic Liquids with Carbon Dioxide, Ind. Eng. Chem. Res., 50:111-118 (2011), American Chemical Society.
Ten (10) pages of International Search Report and Written Opinion dated Oct. 7, 2014, issued in International Application Serial No. PCT/US/2014/028973 filed Mar. 14, 2014.

* cited by examiner

US 9,871,270 B2

FUNCTIONALIZED IONIC LIQUIDS AND THEIR APPLICATIONS

RELATED APPLICATIONS

This Application is a divisional of copending U.S. application Ser. No. 14/213,428, filed Mar. 14, 2014, which claims priority from U.S. Application Ser. No. 61/787,788, filed on Mar. 15, 2013 which are incorporated in entirety by reference.

STATEMENT REGARDING FEDERALLY SPONSORED RESEARCH OR DEVELOPMENT

This work was supported by the Government of the United States of America under Contract No. W911QY-13-P-0472, awarded by the United States Department of Defense, and, Contract No. DE-SC0008265, awarded by the United States Department of Energy. The Government of the United States of America has certain rights in this invention.

FIELD

This disclosure relates to synthesis of new ionic liquids containing amine and alcohol groups and their applications.

This disclosure provides details about the synthesis of new type of ionic liquids functionalized with primary, secondary or tertiary amine groups along with hydroxyl groups in the sample molecule.

This disclosure provides details on the application amine and hydroxyl functionalized ionic liquid in carbon dioxide absorption.

This disclosure provides details on the application amine and hydroxyl functionalized ionic liquid in flame resistant articles.

BACKGROUND

In this section, we discuss several aspects of related work, including background and conventional technologies.

Ionic liquids by definition are salts that have melting points below 100 degree C. Interest in ionic liquids has grown markedly in recent years because of their potential applications in a wide range of fields including, Electroplating, Lubricant, Antistatic coating, Cleaning, Powder coating, Fire resistant treatment, Electrolytes in supercapacitors, fuel cells, lithium ion batteries, and lithium batteries, separations techniques such as Liquid-liquid extraction, Treatment of nuclear waste, Desulfurization of Diesel, Metal extraction, Gas purification and Membranes, solvents or reaction medium in Organic reactions, Acid catalysis, Immobilization catalyst in Synthesis of nanoparticles, in biotechnology applications such as Biomass conversion, Protein purification and Enzymatic reactions, Matrices of mass spectroscopy, and Chromatography and solvents for carbon dioxide capture, sulfur dioxide capture and hydrogen sulfide capture.

Ionic liquids are mainly composed of organic cations, such as alkylammonium, alkylphosphonium, alkylsulfonium, 1,3-dialkylimidazolium, alkyltriazolium, alkylpyridinium, etc. and mononuclear anions, such as $BF_4$, $PF_6$, $CF_3SO_3$, $(CF_3SO_2)_2N$, methide, $CF_3CO_2$. Some ionic liquids containing non-fluoroanions, such as nitrate, perchlorate, alkyl sulfate and alkyl oligoether sulfate, dinitramide, amino acid anions. A variety of organic anions, have also been synthesized and studied. The chemical structure of the typical cations and anions comprised by ionic liquids are provided in FIG. 1

The chemistry of cation and the anion determines the physical and chemical properties of an ionic liquid. Therefore, it is possible to achieve specific physical property by choosing the proper combination of a cation and an anion. For example, the viscosities can be adjusted over a wide range of less than 50 cP to greater than 10,000 cP.

Carbon Dioxide Absorption by Ionic Liquids

There are two types of ionic liquids currently pursued in research field (1) Room temperature ionic liquids (RTILs), and (2) Task-specific or functionalized ionic liquids. High-pressure phase behavior of carbon dioxide with a variety of ionic liquids was first reported back in 2001 by Blanchard et al. Their study included ionic liquids, 1-n-butyl-3-methylimidazolium hexafluorophosphate, 1-n-octyl-3-methylimidazolium hexafluorophosphate, 1-n-octyl-3-methylimidazolium tetrafluoroborate, 1-n-butyl-3-methylimidazolium nitrate, 1-ethyl-3-methylimidazolium ethyl sulfate, and N-butylpyridinium tetrafluoroborate. The researchers observed that a large quantity of carbon dioxide could be dissolved in the ionic liquid phase.

This research group also latter showed that ionic liquids with the bis(trifluoromethylsulfonyl) imide anion had the largest affinity for carbon dioxide regardless of whether the cation was imidazolium, pyrrolidinium, or tetraalkylammonium. These results suggest that the nature of the anion has the most significant influence on the carbon dioxide solubility. The solubility of carbon dioxide in a series of imidazolium-based room-temperature ionic liquids has been determined by Baltus et al.

With the aim of finding ionic liquids that improve carbon dioxide solubility and to understand how to design carbon dioxide-philic ionic liquids, Muldoon et al. studied the low- and high-pressure measurements of carbon dioxide solubility in a range of ionic liquids possessing structures likely to increase the solubility of carbon dioxide. They examined the carbon dioxide solubility in a number of ionic liquids with systematic increases in fluorination. They also found that the anion plays a key role in determining carbon dioxide solubility in ionic liquids in agreement with other research reports.

Thus the literature reports indicate that fluoride containing anions bis[trifluoromethyl sulfonyl] amide and tris (trifluoro methyl sulfonyl) methide [methide] are most suitable as anions in the new ionic liquids for carbon dioxide capture.

The viscosity of common room temperature ionic liquids is quite high. For example, 1-n-butyl-3-methylimidazolium tetrafluoroborate (79.5 cP) is found to be 40 times more viscous as compared to 30 percent monoethanolamine solution at the same temperature (33 Cp). In order to meet the viscosity constraints, ionic liquids can be mixed with some common organic solvents or water. However, inclusion of such liquids will accompany their own drawbacks as well or this may be accomplished at the expense of decrease in gas capture ability. For example, addition of polyethylene glycol to an ionic liquid decreased the carbon dioxide solubility.

Without wishing to bind by any theory, based on the above discussion following conclusions can be arrived: (a) Room temperature ionic liquids themselves have shown adequate level of carbon dioxide solubility and (b) Mixing chemically absorbing species such amines, alcohols and amino alcohols with ionic liquids can shift the equilibrium towards higher carbon dioxide absorption even at low carbon dioxide partial pressures Chemical Structural Features Crucial for Carbon Dioxide Absorption There are over $10^{18}$ ionic liquids available for exploration. It is not practical to synthesize every one of these compounds and select the best ionic liquid for carbon dioxide absorption/Therefore, ionic liquids containing cations in which amino and alcohol functional groups present in the same molecule was judiciously selected. The rationale behind this selection of these functional groups is discussed below.

The state-of-the-art technology for carbon dioxide capture is reversible chemical absorption into an aqueous amine solution. The capacity of an aqueous amine solution to chemically absorb carbon dioxide is a function of the route by which carbon dioxide reacts with the amine. There are two chemical routes generally considered for chemical absorption of carbon dioxide by amines.

Route 1 (carbamate formation—Amine:carbon dioxide=2:1)

Amines can react with carbon dioxide to form a carbamic acid ($R_2NCOOH$).

$$CARBON\ DIOXIDE+R_2NH \rightarrow R_2NCOOH$$
(carbamic acid)

Depending upon its acidity, it may then give up a proton to a second amine molecule forming a carbamate ($R2NCOO^-$).

$$R_2NCOOH \rightarrow R2NCOO^- + H^+ + A$$

second amine molecule may be consumed by the proton liberated from carbamic acid forming carbamate.

$$R_2NH + H^+ \rightarrow R2NH2^+$$

Therefore for every carbon dioxide molecule, two amine molecules are used up. (2:1 ratio). Kinetically and thermodynamically this reaction pathway is generally favored for primary and secondary amines.

Route 2 (proton accepting base—Amine:CARBON DIOXIDE=1:1)

A second reaction route for carbon dioxide absorption is carbon dioxide hydration to form bicarbonate. In this pathway an amine molecule simply acts as a proton accepting base for the hydration of carbon dioxide. The overall stoichiometry for this second pathway is $$carbon\ dioxide + water \rightarrow HCO_3^- + H^+$$

$$R_3N + H^+ \rightarrow R_3H^+$$

According to the route 2, one mole of amine is consumed per mole of carbon dioxide, so in terms of absorption capacity it is more efficient. For tertiary and some sterically hindered primary and secondary amines this is the only pathway contributing to absorption. However, this pathway is generally less favorable kinetically than carbamate formation.

If the carbamic acid formed is a weak acid (higher pKa value) the extent of dissociation to form carbamate is low. Then the route 1 approaches a 1:1 carbon dioxide:amine molar stoichiometry because the carbamate does not deprotonate and consumes a second amine molecule. What type of amines can have higher carbon dioxide absorption capacity (1:1 carbon dioxide:amine ratio). This question was answered by Pauxty et al.

Pauxty et al. have studied the carbon dioxide absorption capacity of 76 different amines. Among these, seven amines, consisting of one primary, three secondary, and three tertiary amines, were identified as exhibiting excellent absorption capacities. Following discussion is based on the publication by Pauxty et al.

According to Pauxty et al. the most interesting result is that all of these amines, share a common structural feature, a hydroxyl group within 2 or 3 carbons of the amine functionality. While it is unclear what the role of this structural feature is, the distance of the hydroxyl functionality from the amine and the structural features around it appears crucial. For example, 2-piperidineethanol and 2-piperidinemethanol achieved capacities of near 1, whereas 3-piperidinemethanol only achieved a capacity of 0.8. This indicates that the proximity of the hydroxyl group and its freedom to move are important.

According to Pauxty et al. one possibility is that a hydroxyl group the appropriate distance from the amine functionality, and with the appropriate structural features surrounding it, is able to form a stable intramolecular hydrogen bond with the nitrogen to form a five or six member ring structure. Intramolecular hydrogen bond formation between amine and hydroxyl groups may decrease the amine pKa, for primary and secondary amines it may also destabilize carbamate formation and push the absorption toward the more stoichiometrically efficient route 2.

Therefore ionic liquids consisting of cations with hydroxyl groups at 2 or 3 carbon from amino groups have been synthesized.

Flame Retardant Ionic Liquids

Flame retardants for textile application have been reviewed by Weil and Levchik. They have provided historical details as well as current FR treatments of textile fabrics. Some of the common FR treatments to fabrics are summarized below based on this review article. Most common FR treatment of cotton fabrics is based on ammonium pyrophosphates. They impart self-extinguishing property to cotton fabrics. Borax is another common flame retardant agent used on fabrics. These treatments are temporary due to their solubility in water.

Polymers containing 35-45% bromine, poly(pentabromobenzyl acrylate) are used as a durable FR treatment on cotton and polyester fabrics. The FR property also can be improved by the addition of antimony oxide.

In recent years, halogen-free, low smoke, and fume flame-retardant composites are becoming of increasing importance, because halogen-type flame retardants can cause problems, such as toxicity, corrosion, and smoke. This has promoted the development of halogen-free, flame-retardant materials. Prior efforts have shown that metal hydroxides are nontoxic and smoke-suppressing additives with a high decomposition temperature in flame-retardant polymeric materials.

The FR material based on tetrakis(hydroxymethyl)phosphonium cation is the most widely sold commercial FR treatment product to date. It is generally agreed that ammonium and phosphonium salts have superior FR properties.

The above described FR treatments of fabrics are either non-durable or inefficient. Ionic liquids have excellent thermal stability and fire resistant properties. They are commercially available and also can be synthesized easily in an industrial scale.

The burning process consists of heating from an external source, decomposition of fabric, combustion of flammable chemicals released from the burning fabric, and propagation of flame.

Burn process starts from an external source of fire. When sufficient heat is applied the fabric starts decomposing. The pyrolysis of fabric (cellulose) results in the release of Levoglucosan and its volatile combustible fragments such as alcohols, aldehydes, ketones, and hydrocarbons. These flammable chemicals burn and propagate the flame and generate more heat. This process perpetuates until the fabric is completely consumed by fire. Part of the decomposition products from the fabric also produce a carbonized residue (char) that does not burn readily. The decomposition of cellulose can be expressed by the following equation:

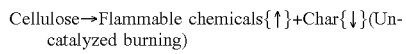
Cellulose→Flammable chemicals{↑}+Char{↓}(Uncatalyzed burning)

A flame retardant alters (catalyzes) the decomposition path of cellulose so that the amount of flammable chemicals is reduced and the amount of char formed is increased.

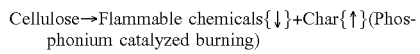
Cellulose→Flammable chemicals{↓}+Char{↑}(Phosphonium catalyzed burning)

The ammonium and phosphonium flame retardants generally lower the decomposition temperature of cellulose and promote dehydration of the cellulose during thermal stress. Phosphorus-containing compounds increase the amount of carbon by redirecting chemical reactions involved in the decomposition. As more carbon is produced, the yields of volatile and flammable aldehydes and ketones are reduced. Ammonium based flame retardants also function through a similar mechanism.

In general, nylon fabrics have low flammability than cotton fabrics. Typical low weight nylon fabric melts and drips away, when exposed to flame and stops the propagation of flame.

Nylon Cotton (NYCO) fabrics are made using a 50% nylon/50% cotton blend and pirovide combat utility uniforms with excellent comfort and durability. However, NYCO fabrics have no flame resistant (FR) properties. Therefore for flame retardant fabrics one has to rely on expensive specialty fibers. Instead of using expensive fabrics, it will be economical to impart FR property on the NYCO fabric by treating them with flame resistant materials/coatings. The FR treatment should not deteriorate the fabric strength and should not add stiffness and significant weight to the fabric.

Ionic liquids containing ammonium and phosphonium cations exhibit exceptional flame resistant properties. In addition, they are non-flammable, high temperature stable (>250 degree C.), non-volatile liquids and amenable to coating on textile fabrics. Unlike conventional FR chemicals, ionic liquids are generally colorless and do not interfere with the other properties of the military fabrics such as camouflage. Along with flame resistant property ionic liquids also have added advantage of multi-functional capabilities such as antistatic, conductive and antimicrobial properties. In spite of these excellent multifunctional properties, ionic liquids are not widely used in fabric treatment due to the lack of detailed studies on the ionic liquid coatings on textiles.

Amino and hydroxy functional groups in the ionic liquid molecules can interact with the textile fabrics and can strongly bind to the fabric. This will increase the durability of the ionic liquids treated fabrics for several washings Ionic Liquids as Electrolytes and Flame Retardant Additives to Electrolytes in Lithium Ion Batteries Even though, energy storage capacity of lithium ion-batteries is superior to other rechargeable battery chemistries, safety issues related with the lithium-ion batteries are the major hindrance for their application as high power batteries. The low boiling organic solvents used as the electrolytes are the main cause of the safety concerns. These solvents have a flash point around 30° C. and could easily catch fire if vented from a hot battery. Moreover, the electrolytes decompose on contact with the charged active materials, both anodes and cathodes. At the end of the charging as well as at high temperatures, the cathode dissolves which accelerates the electrolyte decomposition. When a cell is heated above 130° C., exothermic chemical reactions between the electrolyte and electrodes trigger thermal run away reactions which are a serious safety hazard. Hence, high power lithium-ion batteries are developed with various external safety devices like current limiting devices, fuses, circuit breakers etc. These devices increase the cost and complexity of the battery module and also consume substantial power.

Considering these safety hazards, development of non-flammable, low volatile, thermally as well as electrochemically stable lithium battery electrolytes are essential for the use of high power lithium batteries in aviation. In this context, "ionic liquids" (ILs) which are liquids at room temperature composed of ions as the electrolytes for high power lithium batteries look extremely attractive. Pyrrolidinium based room temperature ionic liquids have been widely investigated as electrolytes in lithium batteries because of their low viscosities and reasonable conductivities. These ionic liquids are 'non-flammable' chemicals but are not 'flame-retardants'. Uncontrolled thermal reactions in high-energy density lithium batteries may lead to fire and pyrrolidinium based ionic liquids cannot withstand these extreme conditions. This scenario undercuts the original reason for employing ionic liquids as electrolytes even by compromising on their low conductivity compared to organic carbonate based electrolytes. Therefore, alternate ionic liquids need to be developed which exhibit high ionic conductivity and non-flammability and are capable of quenching the fire in case of short circuits, local heating and or in abuse conditions such as overcharging.

Ionic Liquids for Corrosion Protection

Ionic liquids as desiccants and chloride removal system—Corrosion is a critical problem for the aircrafts. It costs Department of Defense over $10 billion year just in maintenance of equipment's and installations. Corrosion is not only a cost issue, but it also impacts our troop's readiness, safety and their performance. The effect of corrosion felt by the Air Force most because aircraft structures are mostly made of metal. Corrosion is usually battled with special alloys and a variety of corrosion protection coatings. However, there is no 'silver bullet' available to completely eliminate the corrosion problem. The corrosion issue can be alleviated if the environmental factors that hasten the corrosion of metal alloys can be addressed properly. Two important factors that affect metals in an aircraft are humidity and chloride content in the atmosphere. Currently humidity level in an aircraft is controlled with the help of dehumidifiers. However, chloride deposition on the aircraft parts requires special attention. Because, desiccants used in the humidity control system are not effective against chloride accumulation. Therefore, new efficient desiccants that not only dehumidify the environment but also remove chloride ions from air are needed.

Ionic liquid based desiccant systems are capable of both humidity control and chloride removal. Ionic liquids are non-volatile liquids as well as efficient desiccants. The ionic liquids can be functionalized to remove chloride ions from the environment.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

SUMMARY

Disclosure provided an ionic liquid represented by the structure of the following Formula 1:

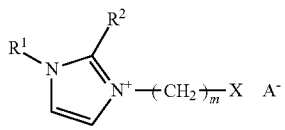

Formula 1 wherein
(a) $R^1$ and $R^2$ are each independently H, or a $C_1$ to $C_{12}$ straight-chain alkyl group or branched alkyl group or aryl group,
(b) m is an integer 1 to 6,
(c) X is $-N(R^3)-(CH_2)_q-OH$, wherein $R^3$ is H or $C_1$ to $C_6$ straight-chain or branched alkyl group and q is an integer from 2 to 4, and
(d) $A^-$ is an anion selected from the group consisting of $[BF_4]^-$, $[PF_6]^-$, $[CH_3CO_2]^-$, $[HSO_4]^-$, $[CF_3SO_3]^-$, $[(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

Disclosure provides a fire retardant coating for textile fabrics. The fire retardant has the ionic liquid of Formula 1. Disclosure provides a solvent for carbon dioxide capture. The solvent includes the ionic liquid of Formula 1. Disclosure provides an electrolyte in a lithium ion battery. The electrolyte includes the ionic liquid of Formula 1. Disclosure provides a flame retardant additive to an electrolyte in a lithium ion battery. The flame retardant additive includes the ionic liquid of Formula 1. Disclosure provides an electrolyte in a metal air battery. The electrolyte includes the ionic liquid of Formula 1. Disclosure provides a flame retardant additive to an electrolyte in a metal air battery. The flame retardant additive includes the ionic liquid of Formula 1.

Disclosure provides an ionic liquid represented by the structure of the following Formula 2:

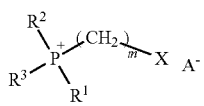

Formula 2 wherein
(a) $R^1$ and $R^2$ are each independently H, or a $C_1$ to $C_{12}$ straight-chain alkyl group or branched alkyl group or aryl group,
(b) m is an integer 1 to 6,
(c) X is $-N(R^3)-(CH_2)_q-OH$, wherein $R^3$ is H or $C_1$ to $C_6$ straight-chain or branched alkyl group and q is an integer from 2 to 4, and,
(d) $A^-$ is an anion selected from the group consisting of $[BF_4]^-$, $[PF_6]^-$, $[CH_3CO_2]^-$, $[HSO_4]^-$, $[CF_3SO_3]^-[(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

Disclosure provides a fire retardant coating for textile fabrics. The fire retardant includes the ionic liquid of Formula 2. Disclosure provides a solvent for carbon dioxide capture. The solvent includes the ionic liquid of Formula 2. Disclosure provides an electrolyte in a lithium ion battery. The electrolyte includes the ionic liquid of Formula 2. Disclosure provides a flame retardant additive to an electrolyte in a lithium ion battery. The flame retardant additive includes the ionic liquid of Formula 2. Disclosure provides an electrolyte in a metal air battery. The electrolyte includes the ionic liquid of Formula 2. Disclosure provides a flame retardant additive to an electrolyte in a metal air battery. The flame retardant additive includes the ionic liquid of Formula 2.

Disclosure provides an ionic liquid having a flame retardant property. The ionic liquid is represented by Formula 3:

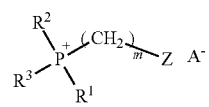

Formula 3 wherein
(a) $R^1$ and $R^2$ are each independently H, or a $C_1$ to $C_{12}$ straight-chain alkyl group or branched alkyl group or aryl group,
(b) m is an integer 1 to 6,
(c) Z is $-OH$ or $NR^3R^4$, where $R^3$ and $R^4$ are each independently H or $C_1$ to $C_6$ straight-chain or branched alkyl group, and,
(d) $A^-$ is an anion selected from the group consisting of $[BF_4]^-$, $[PF_6]^-$, $[CH_3CO_2]^-$, $[HSO_4]^-$, $[CF_3SO_3]^-[(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid, and wherein the ionic liquid has flame retardant property.

Disclosure provides a fire retardant coating for textile fabrics. The fire retardant coating includes the ionic liquid of Formula 3. Disclosure provides an electrolyte in a lithium ion battery. The electrolyte includes the ionic liquid of Formula 3. Disclosure provides a flame retardant additive to an electrolyte in a lithium ion battery. The flame retardant additive includes the ionic liquid of Formula 3. Disclosure provides an electrolyte in a metal air battery. The electrolyte includes the ionic liquid of Formula 3. Disclosure provides a flame retardant additive to an electrolyte in a metal air battery. The flame retardant additive includes the ionic liquid of Formula 3.

Disclosure provides a method of preparing the ionic liquid of Formula 1. The method includes refluxing the compound having Formula 4 with an amino alcohol and potassium carbonate in the presence of a solvent to obtain the ionic liquid of Formula 1. Formula 4 is represented by the following structure

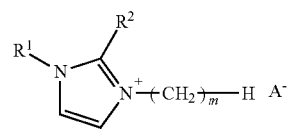

Formula 4 wherein
(a) $R^1$ and $R^2$ are each independently H, or a $C_1$ to $C_{12}$ straight-chain alkyl group or branched alkyl group or aryl group,
(b) m is an integer 1 to 6,
(c) H is Cl, Br, I,
(d) $A^-$ is $Cl^-$, $Br^-$, $I^-$.

Disclosure provides a method of preparing the ionic liquid of Formula 2. The method includes refluxing the compound represented by the Formula 5 with an amino alcohol and potassium carbonate in a solvent to obtain the ionic liquid of Formula 4. Formula 5 is represented by the following structure

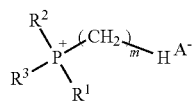

Formula 5 wherein
(a) $R^1$ and $R^2$ are each independently H, or a $C_1$ to $C_{12}$ straight-chain alkyl group or branched alkyl group or aryl group,
(b) m is an integer 1 to 6,
(c) H is Cl, Br, I, and,
(d) $A^-$ is $Cl^-$, $Br^-$, $I^-$.

Disclosure provides a flame retardant fabric product having a fabric, a flame retardant ionic liquid represented by Formula 3, and a binder. About 1% to about 60% by weight of the flame retardant fabric product is made up of the flame retardant ionic liquid. The fabric can be Cotton, Cellulose, Rayon, Nylon, Polyester, Polyurethane Polyamide, and aramid.

Disclosure provides a method of preparing the flame retardant fabric. The method includes coating the fabric with the flame retardant ionic liquid represented by Formula 3 and the binder to obtain a coated fabric. The coated fabric is cured at a temperature of about 20 degree C. to about 300 degree C. for about 1 minute to about 12 hours to obtain the flame retardant fabric.

BRIEF DESCRIPTION OF THE DRAWINGS

The above objectives and advantages of the disclosed teachings will become more apparent by describing in detail preferred embodiments thereof with reference to the attached drawings in which.

DETAILED DESCRIPTION

Figure 1:
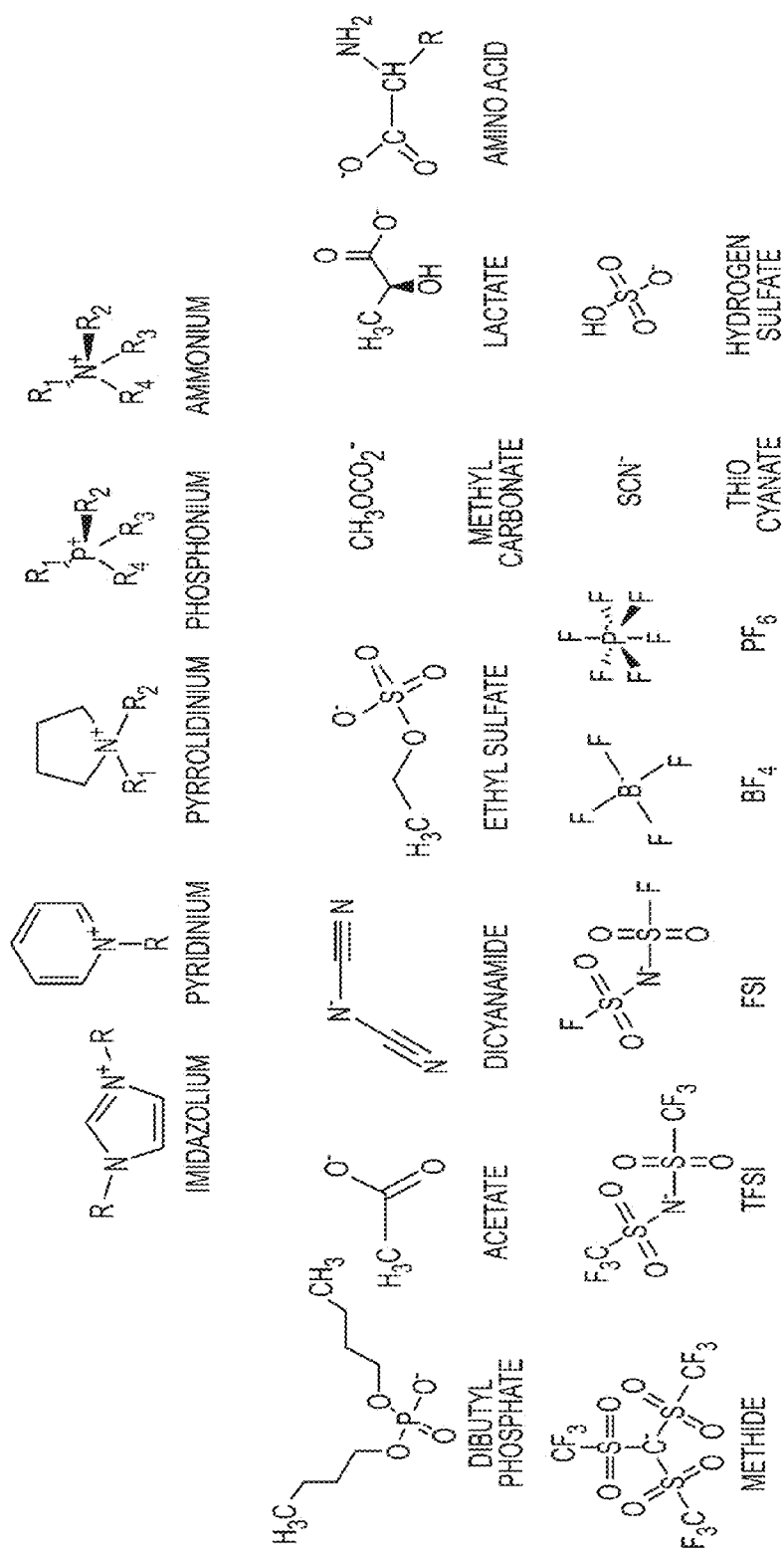
FIG. 1. Chemical structure of typical cations and anions of ionic liquid.

It is an object of the present disclosure to provide amino alcohol functionalized ionic liquid compounds, compositions together with methods for their synthesis and their use.

It is an object of the present disclosure to provide an ionic liquid with structural moiety consisting of a hydroxyl group or hydroxyl groups within 2 or 3 carbons of the amine functional group.

It is an object of the present disclosure to provide an ionic liquid of Formula 1:

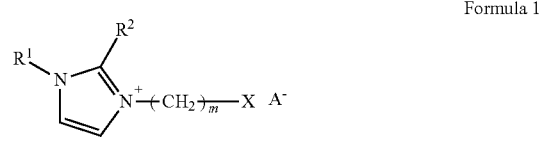

Formula 1 wherein
(a) $R^1$ and $R^2$ are each independently H, or a $C_1$ to $C_{12}$ straight-chain alkyl group or branched alkyl group or aryl group,
(b) m is an integer 1 to 6,
(c) X is $-N(R^3)-(CH_2)_q-OH$ where $R^3$ is H or $C_1$ to $C_6$ straight-chain or branched alkyl group and q is an integer from 2 to 4, and
(d) $A^-$ is an anion selected from the group consisting of $[BF_4]^-$, $[PF_6]^-$, $[CH_3CO_2]^-$, $[HSO_4]^-$, $[CF_3SO_3]^-[(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

Disclosure provides a fire retardant coating for textile fabrics. The fire retardant has the ionic liquid of Formula 1. Disclosure provides a solvent for carbon dioxide capture. The solvent includes the ionic liquid of Formula 1. Disclosure provides an electrolyte in a lithium ion battery. The electrolyte includes the ionic liquid of Formula 1. Disclosure provides a flame retardant additive to an electrolyte in a lithium ion battery. The flame retardant additive includes the ionic liquid of Formula 1. Disclosure provides an electrolyte in a metal air battery. The electrolyte includes the ionic liquid of Formula 1. Disclosure provides a flame retardant additive to an electrolyte in a metal air battery. The flame retardant additive includes the ionic liquid of Formula 1.

It is an object of the present disclosure to provide an ionic liquid represented by the structure of the Formula 2:

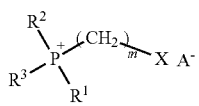

Formula 2 wherein
(a) $R^1$ and $R^2$ are each independently H, or a $C_1$ to $C_{12}$ straight-chain alkyl group or branched alkyl group or aryl group
(b) m is an integer 1 to 6
(c) X is $-N(R^3)-(CH_2)_q-OH$ wherein $R^3$ is H or $C_1$ to $C_6$ straight-chain or branched alkyl group and q is an integer from 2 to 4; and
(d) $A^-$ is an anion selected from the group consisting of $[BF_4]^-$, $[PF_6]^-$, $[CH_3CO_2]^-$, $[HSO_4]^-$, $[CF_3SO_3]^- [(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

Examples of 'X' include but not limited to monoethanol amine, diethanol amine, N-methyl ethanolamine 2-amino-2-methyl-1,3-propanediol, 2-piperidineethanol, 2-piperidinemethanol, diisopropanol amine, 3-quinuclidinol, N,N-dimethylethanolamine, and 3-piperidino-1,2-propandiol groups.

It is an object of the present disclosure to provide a solvent composition containing a mixture of amine functionalized ionic liquids with alcohol functionalized ionic liquids.

It is an object of the present disclosure to use functionalized ionic liquids as solvents for carbon dioxide capture.

It is an object of the present disclosure to use functionalized ionic liquids as fire retardant coating on articles including textile fabrics.

It is an object of the present disclosure to use functionalized ionic liquids as desiccants to remove moisture and chloride and other corrosive chemicals.

It is an object of the present disclosure to use functionalized ionic liquids as solvents in organic reactions.

It is an object of the present disclosure to use functionalized ionic liquids as electrolyte in metal batteries including lithium ion batteries, and metal air batteries.

It is an object of the present disclosure to use functionalized ionic liquids as additive to electrolyte in metal batteries including lithium ion batteries, and metal air batteries.

It is an object of the present disclosure to use functionalized ionic liquids as a medium for electro deposition of metal coating including nickel and cobalt coatings.

It is an object of the present disclosure to use functionalized ionic liquids as a solvent or medium for coating powders.

It is an object of the present disclosure to use functionalized ionic liquids as a solvent or medium for preparing nano powders including nano metal powders and nanometal oxide powders.

It is an object of the present disclosure to use functionalized ionic liquids as a scrubbing material for desulfurization.

Disclosure provides a fire retardant coating for textile fabrics. The fire retardant includes the ionic liquid of Formula 2. Disclosure provides a solvent for carbon dioxide capture. The solvent includes the ionic liquid of Formula 2. Disclosure provides an electrolyte in a lithium ion battery. The electrolyte includes the ionic liquid of Formula 2. Disclosure provides a flame retardant additive to an electrolyte in a lithium ion battery. The flame retardant additive includes the ionic liquid of Formula 2. Disclosure provides an electrolyte in a metal air battery. The electrolyte includes the ionic liquid of Formula 2. Disclosure provides a flame retardant additive to an electrolyte in a metal air battery. The flame retardant additive includes the ionic liquid of Formula 2.

It is an object of the present disclosure to use an ionic liquid represented by the structure Formula 3 of the as a flame retardant compound.

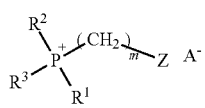

Formula 3 wherein
(a) $R^1$ and $R^2$ are each independently H, or a $C_1$ to $C_{12}$ straight-chain alkyl group or branched alkyl group or aryl group
(b) m is an integer 1 to 6
(c) Z is $-OH$ or $NR^3R^4$ wherein $R^3$ and $R^4$ are each independently H or $C_1$ to $C_6$ straight-chain or branched alkyl group
(d) $A^-$ is an anion selected from the group consisting $[BF_4]^-$, $[PF_6]^-$, $[CH_3CO_2]^-$, $[HSO_4]^-$, $[CF_3SO_3]^- [(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

Disclosure provides a fire retardant coating for textile fabrics. The fire retardant coating includes the ionic liquid of Formula 3. Disclosure provides an electrolyte in a lithium ion battery. The electrolyte includes the ionic liquid of Formula 3. Disclosure provides a flame retardant additive to an electrolyte in a lithium ion battery. The flame retardant additive includes the ionic liquid of Formula 3. Disclosure provides an electrolyte in a metal air battery. The electrolyte includes the ionic liquid of Formula 3. Disclosure provides a flame retardant additive to an electrolyte in a metal air battery. The flame retardant additive includes the ionic liquid of Formula 3.

It is another object of the present disclosure is to provide a method of preparing the ionic liquid represented by the formula 1. The method includes refluxing the compound represented by the Formula 4 with an amino alcohol and potassium carbonate.

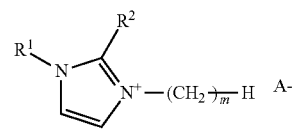

Formula 4 wherein
(a) $R^1$ and $R^2$ are each independently H, or a $C_1$ to $C_{12}$ straight-chain alkyl group or branched alkyl group or aryl group
(b) m is an integer 1 to 6
(c) H is Cl, Br, I
(d) $A^-$ is $Cl^-$, $Br^-$, $I^-$.

It is another object of the present disclosure is to provide a method of preparing the ionic liquid of claim 8, The method includes refluxing the compound represented by the Formula 5 with an amino alcohol.

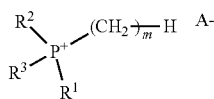

Formula 5 wherein (a) $R^1$ and $R^2$ are each independently H, or a $C_1$ to $C_{12}$ straight-chain alkyl group or branched alkyl group or aryl group (b) m is an integer 1 to 6

(c) H is Cl, Br, I (d) $A^-$ is $Cl^-$, $Br^-$, $I^-$. Refluxing also requires potassium carbonate.

Carbon Dioxide Capture by Functionalized Ionic Liquids

There is increasing concern for the reduction of CO2 emissions from flue and fuel gas operations because these emissions have resulted in global climate change and a significant increase in global warming due to the "greenhouse gas (GHG) effect". Approximately 83% of the GHG emissions in the U.S. are produced from combustion and nonfuel uses of fossil fuels. One approach that holds great promise for reducing GHG emissions is carbon capture and sequestration (CCS). Under this concept, CO2 would be captured from large point sources, such as power plants, and injected into geologic formations. This approach would lock up (sequester) the CO2 for thousands of years. DOE's Carbon Sequestration Program that is managed by the National Energy Technology Laboratory (NETL), is pursuing various technological approaches aimed at reducing GHG emissions.

Aqueous amine absorption is the state-of-the-art technology that is used to separate and capture CO2 from flue gas streams produced by existing coal-fired electric generating power plants. However, the use of amines for CO2 absorption has some disadvantages, including (i) high energy requirement for solvent regeneration, (ii) their high vapor pressure and subsequent mass loss through evaporation, (iii) degradation of the solvent and associated plant corrosion, and (iv) significant capital and operating costs. On the other hand, solvent regeneration is easier and less energy intensive with physical adsorption of CO2. Physical absorption has generally lower absorption capacity when compared to chemical absorption under low CO2 partial pressures.

The concept of using ionic liquids (IL's) as potential alternatives to aqueous alkanolamines for CO2 capture has recently gained considerable interest. IL's have advantages that include negligible vapor pressure, higher thermal stability and lower heat capacity. In addition, like alkanolamines they have fast capture kinetics and low viscosity. In order to take advantage of the useful properties of IL's for post-combustion CO2 capture, functionalized-IL's to be investigated as potential replacement solvents for aqueous amine scrubbing systems.

This disclosure provides routes for synthesizing amino-alcohol functionalized ionic liquids and evaluated their CO2 capture capacity and regeneration capability. The amino-alcohol functionalized ionic liquids exhibited 20× higher CO2 capture capacity compared to unfunctionalized IL's at low pressures (1 bar). The IL's also demonstrated high thermal stability both in nitrogen and in air. CO2 can be thermally desorbed by heating the IL's to 80-120 degree C. at 1 bar CO2 pressure without significant degradation. The cost and energy performance calculations clearly demonstrated that the IL's disclosed here could be competitive with an amine process if the target parameters such as CO2 capture capacity, viscosity, heat capacity, and cost of the IL are achieved.

The selection of a suitable solvent is vital for the economic viability of the CO2-capture process. The main selection criteria are high solubility of carbon dioxide and, equally important, high absorption selectivity of carbon dioxide over nitrogen. Furthermore, low energy desorption is highly desirable, as it reduces the necessary regeneration temperature and pressure difference. In order to prevent the loss of solvent, a low vapor pressure and high thermal stability as well as long-term stability are beneficial. The cost and environmental toxicity of the solvents have to be considered along with the evaporative loss and chemical degradation characteristics of IL's.

Carbon dioxide absorption data showed that mixing of amino and hydroxy functionalized ionic liquids exhibit higher carbon dioxide absorption. Therefore, synthesizing new ionic liquids containing both hydroxyl and amino groups in a single ionic liquid molecule will result in a better carbon dioxide capturing solvent.

In this disclosure ionic liquids incorporating structural features, that is, hydroxyl group within 2 carbons of the amine functionality, have been synthesized and their CO2 absorption capacity was measured. A maximum of mol CO2/mol IL ratio of 0.4 was obtained. It was observed that subtle changes in the chemical structure could affect the CO2 absorption capacity. For example, by replacing methyl imidazolium with dimethyl imidazolium moiety, the CO2 absorption capacity of IL's increased by ~50%.

Synthesis of Ionic Liquids Containing Amino-Alcohol Functional Groups

A simple and versatile two step path way was developed for synthesizing ionic liquids containing cations with both alcohol and amino functional groups. In the first step bromoalkyl precursor compound of alkyl imidazole or alkyl phosphine was synthesized. For example, methyl imidazole was reacted with 1,3 dibromopropane to from bromopropyl methyl imidazolium bromide as represented in the scheme below:

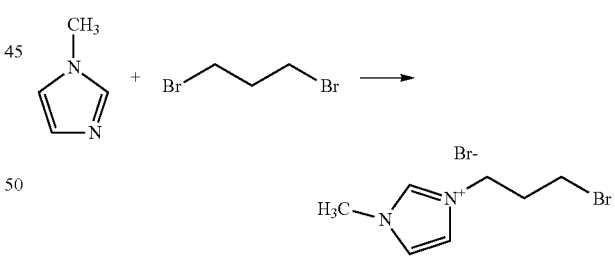

This synthesis process was very versatile in that bromoalkyl imidazolium and bromoalkyl phosphonium precursors can be reacted with any type of alkanol amine compounds to form the corresponding amino alcohol functionalized ionic liquids. For example, reaction with N-methyl ethanolamine is provided below:

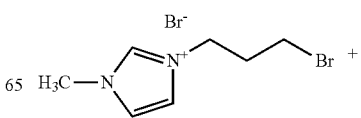

-continued

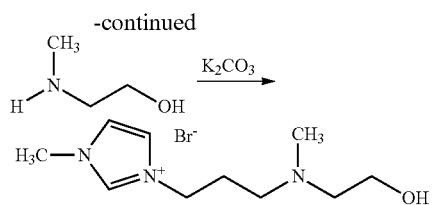

The above synthesis process is simple to scale up. This process can be extended to other types of amino alcohols without any drastic modifications in the reaction conditions. The bromo anions were ion-exchanged with various anions listed in FIG. 1 to form the corresponding ionic liquids.

Figure 2:
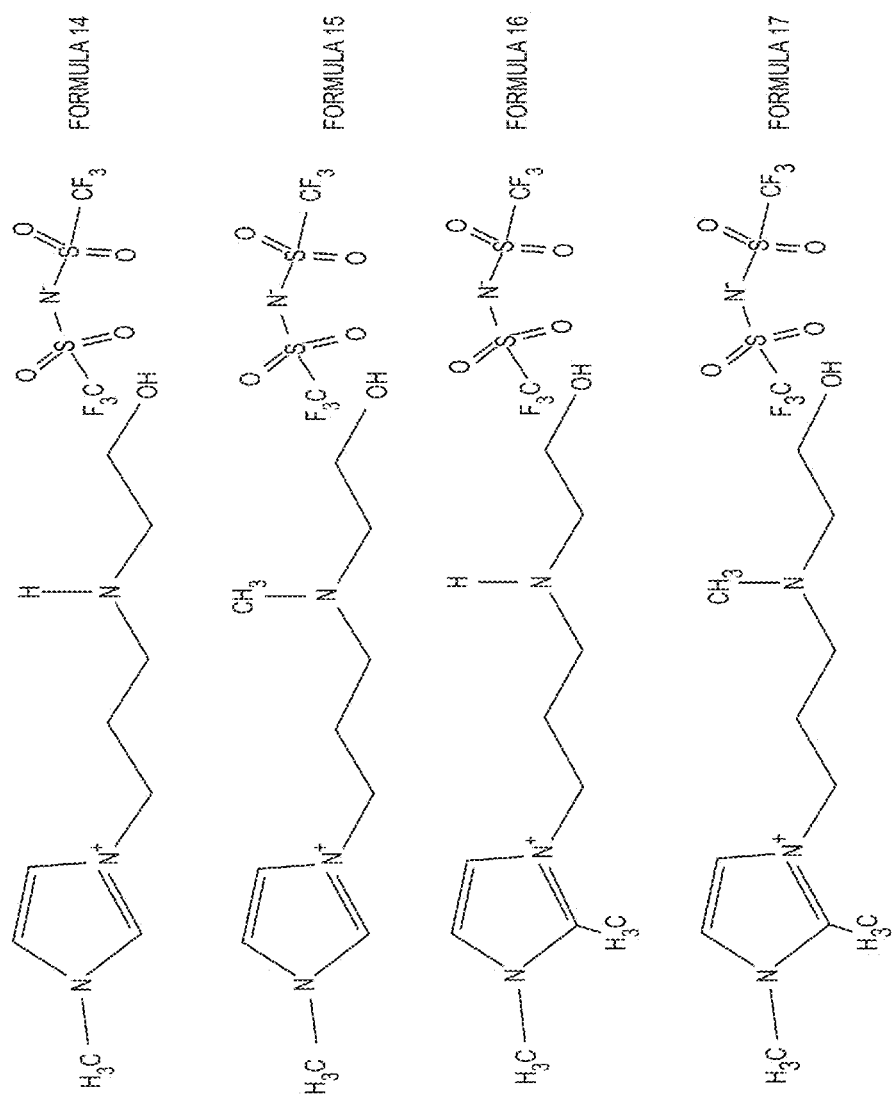
FIG. 2. Chemical structure of representative ionic liquids containing amino alcohol functional groups.

The chemical structure of typical ionic liquids containing cations with amine and alcohol functional groups are provided in FIG. 2.

Thermal Stability of Ionic Liquids

Figure 15:
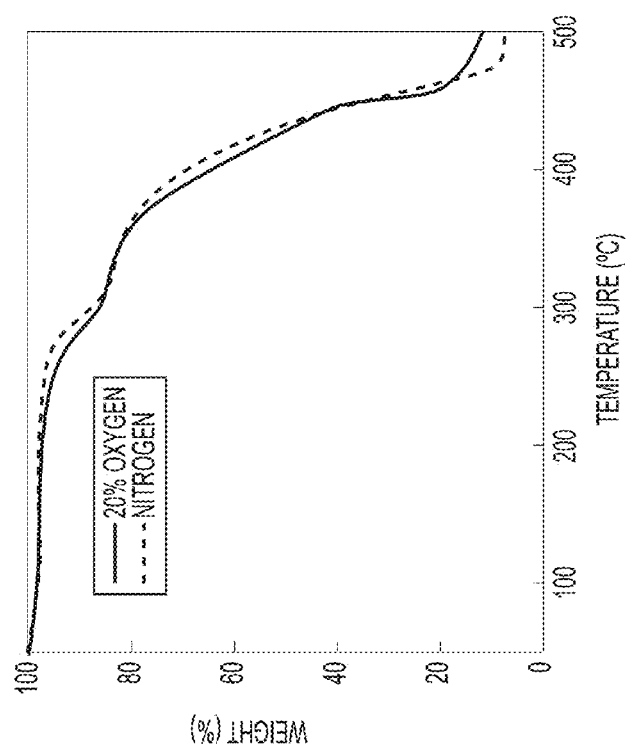
FIG. 15. Thermogravimetric analysis (TGA) plot of formula 7 under the flow of nitrogen and 20% oxygen FIG. 16. CO2 absorption by amino alcohol functionalized ionic liquids in comparison with hexyl methyl imidazolium bis(trifluoromethyl sulfonyl)imide ionic liquid (C6mimNTf2)

In order to determine the thermal stability of the functionalized imidazolium ionic liquids synthesized in the thermogravimetric analysis (TGA) was conducted. The purge atmosphere was either nitrogen or air at 100 ml/min and 10° C./min to 600° C. Typical TGA data under nitrogen and air (20% Oxygen) are provided in FIG. 15. It is important to note that the amino alcohol groups are stable up to 280° C. This stability cannot be achieved by the physical mixing of monoethanol amine (MEA) with an unfunctionalized ionic liquid. Both the curves almost overlap indicating that the disclosed ionic liquids are stable in nitrogen as well as in air up to 280° C.

Carbon Dioxide Absorption Studies

Figure 16:
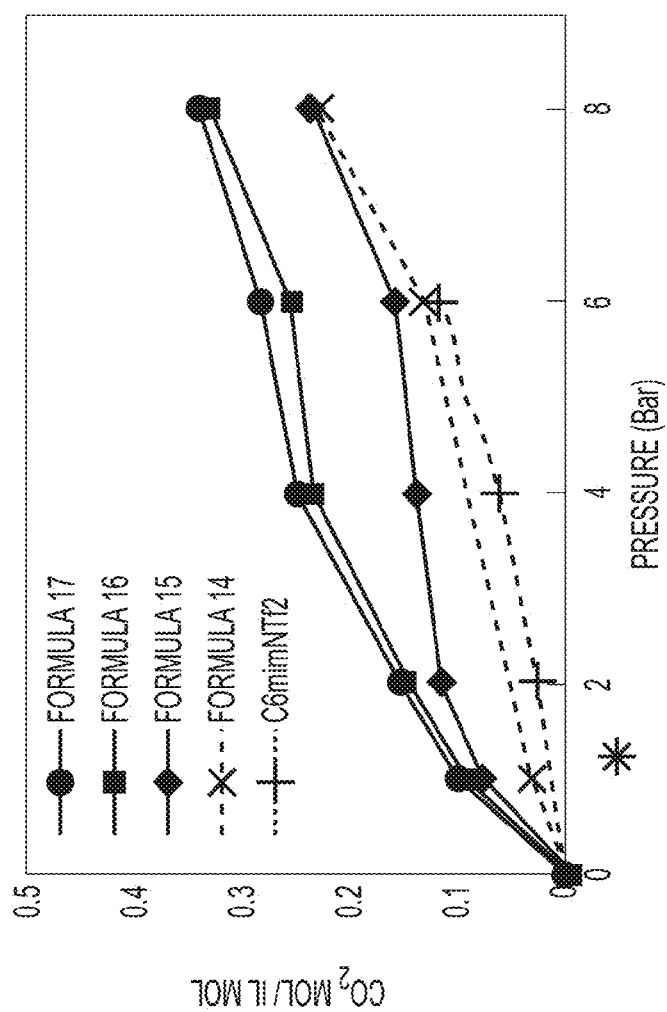

CO2 absorption setup was designed and built in-house to measure the amount of CO2 absorbed by the various IL samples of this disclosure. The ionic liquid samples (about 3 g) were loaded in the isochoric cell and degassed at 80° C. and 3 mbar vacuum for a period of 12-18 h. After cooling the sample to 25° C., CO2 gas was introduced into the isochoric cell. The desired pressure was set at between 0-8 bar. The sample was stilted during the absorption experiment. The weight increase due to CO2 absorption was measured at various exposure times and pressures and plotted in FIG. 16. The total absorption duration was 18 h for all the samples tested. Even after exposing for 18 h, the equilibrium may not have been reached with these ionic liquids due to the slow reaction kinetics and the high viscosity of the solvent. In FIG. 16, CO2 absorption data of functionalized IL's (chemisorption) and 1-hexyl-3-methyl imidazolium bis(trifluoromethyl sulfonyl)imide (C6mimNTf2) (physisorption) are compared.

Viscosity

Upon CO2 absorption of the viscosity of all of these ILs has increased. But the increase in viscosity is marginal compared to the anion functionalized ionic liquids reported by Brennecke et al. For example, Amine-Functionalized Anion-Tethered IL's based on trihexyl(tetradecyl) phosphonium systems exhibited a viscosity increase of 48-240 folds compared <2 fold increase in the amino alcohol functionalized cation ion-tethered systems disclosed here. These results indicate that anion-functionalized IL's exhibit more effect viscosity upon CO2 absorption than cation-functionalized IL's. The viscosities of cation-functionalized IL's disclosed here can be decreased by selecting appropriate anions.

Desorption Data

Ionic liquid represented by the formula 17 was down selected for investigating the stability of CO2 absorption during the recycling of IL. CO2 absorption was carried out at 40° C. for 12 h under 0.15 bar CO2 pressure, and desorption was performed at 80-120° C. under 1 bar CO2 pressure for 30 minutes. These are the typical conditions used in the industrial CO2 scrubber. The absorption capacity of IL remained stable during 15 cycles (100 plus or minus 2%) indicting that the CO2 absorption is reversible.

Most of the studies on NTf2 anion-based IL's were focused on CO2 capture by physisorption mechanism. Based on molecular simulations, it has been suggested that the anions surround the amino groups in the IL's and shield them from reacting with CO2. The bulky NTf2 can be substituted with smaller anions such as BF4 or PF6 or amino acid anions which may not hinder the reaction between amino-alcohol groups and CO2 molecules. BF4 anion containing amino functionalized IL also known to exhibit higher CO2 absorption capacity.

The following is the summary of the CO2 absorption data observed:

1. Amino-alcohol functionalized ionic liquids show higher CO2 absorption capacity (20x) than the unfunctionalized IL's (C6mimNTf2) at low CO2 pressures (1 bar).

2. The absorption of CO2 by ionic liquids represented by the chemical formulae 14, 15, 16 and 17, even at low CO2 pressures (<1 bar), indicates that CO2 is absorbed via a chemisorption mechanism.

3. Dimethyl imidazolium IL's exhibit 2x higher absorption capacity compared to monomethyl imidazolium IL's. This shows even minor modifications in the chemical structure can strongly influence the CO2 absorption property of the IL's.

4. Anions form strong hydrogen bonds with amino groups and organize around the amino-alcohol groups. So, high reactivity and absorption capacity can be achieved by using a different anion which is not hindering the interaction between CO2 molecule and amino-alcohol groups.

5. High viscosity of the functionalized IL's before and after CO2 capture is one of the major hurdles in implementing these IL's in the post combustion CO2 capture process. Viscosity of functionalized IL's decreases with the reduction in the number of protons in the amino group (NH2 (10,000 cP)>NH (4435 cP)>N—CH3 (407 cP)). Substitution of N—C2H5 or N-aliphatic ring for N—H group can help in reducing the viscosity of the IL without decreasing the CO2 absorption.

6. Dilution of functionalized IL's with low viscosity IL solvent is a viable alternative method to alleviate the viscosity problem.

7. The absorption capacity of IL remained stable over 15 cycles of CO2 absorption/desorption indicating reversibility of functionalized IL's.

Flame Retardant Ionic Liquids

This disclosure provided the several ionic liquids based on imidazolium cations and phosphonium cation. Interestingly these ionic liquids exhibited flame retardant (referred in this disclosure as "FR") properties. These ionic liquids are coated onto textile fabrics including but not limited to cotton, nylon, nylon:cotton (50:50) (here onwards referred as 'NYCO"), polyester, polyethylene, polypropylene, polyurethane, for imparting flame retardancy to the fabrics. Durable FR coating can be formed by chemically reacting or physically containing on the surface of the fabric [T. A. Perenich, Protective Clothing: Use of Flame-Retardant Textile Finishes, Ch. 7, Protective Clothing Systems and Materials, Ed. By M. Raheel, Marcel Dekker, (1994)].

These coatings are not removed during repeated washings of at least 1 times preferably up to at least about 25 washings. The FR coatings are typically applied by pad-dry-cure process from the formulations containing FR chemical (ionic liquid in this case) and finishing chemicals such as cross-linking agents.

The FR coating formulation were applied on to the fabric by the following two approaches: (a) Applying directly onto the textile fabric or by using a binder including but not limited to melamine, urea, acrylate, polyurethane, epoxy, polysiloxane, and silane based binders. Simple ionic liquids based on imidazolium or phosphonium cations with appropriate binders were added to the FR coating formulation for better cross-linking of the ionic liquids to fabrics, (b) Second approach was to strongly bind ionic liquids to fabric is using insitu-polymerization to strongly bind around the fibers of the fabric. For insitu-polymerization, monomers such as Acrylamido-2-propane-sulfonic acid (AMPS) with cross-linker N,N'-Methylene bisacrylamide (MBAm) were mixed with ionic liquids in the coating formulation.

Two ionic liquids tetrabutyl phosphonium diethyl phosphate (TPEP) and Ethyl methyl imidazolium diethyl phosphate (EIP) were purchased from IoLiTec Inc., Tuscaloosa, Ala. Acrylamido-2-propane-sulfonic acid (AMPS), cross-linker N,N'-Methylene bisacrylamide (MBAm), Tributyl phosphine, Triethyl amine (TEA), and 1-bromo propanol were purchased from Sigma Aldrich, Saint Louis, Mo. Solvents such as acetonitrile, ether, and methanol were purchased from Pharmo Aaper, Belmont, N.C. 419W style cotton fabric was purchased from Test Fabrics, West Pittston, Pa. Rip-stop weave Nylon 50: Cotton 50 fabrics were supplied by the Brittany Dyeing and Printing Corporation, New Bedford, Mass.

Flame resistance of two ionic liquids tetrabutyl phosphonium diethyl phosphate (TPEP) and Ethyl methyl imidazolium diethyl phosphate (EIP) coated 419W cotton fabrics were measured according to standard test method ASTM 6413-08. The uncoated cotton control fabric was completely consumed by the fire during the test. The ionic liquids TPEP and EIP coated cotton fabrics formed char during flame testing. But it also exhibited higher char length. Their char yield and char length were very high as shown in Table 3 provided in the example 19. The ionic liquids themselves are non-flammable materials but when coated onto cotton fabric they did not protect the fabric from fire. Mixing these two ionic liquids with urea also resulted in poor char yield (less than 42 percent).

Polymerization Coating with AMPS

In order to improve the flame retardant property, the TPEP-coated cotton fabric was coated with a layer of AMPS (30%) monomer and MBAm (3%) cross linker. Then the fabric was air dried for 4 days before the vertical flame testing. Cotton fabric coated with TPEP/AMPS-MBAm was subjected to vertical flame testing. The coated fabric exhibited a less vigorous flame than the uncoated control fabric. After-flame time and char length was also significantly reduced and no afterglow was observed.

The various compositions of AMPS/MBAm polymer coatings gave a clear indication of how effective the coating becomes with different ratios of the monomer and cross linking agent. The lowest char length and highest char yield were observed for the samples coated with a 30% AMPS/6% MBAm solution, with ammonium persulfate (APS) to catalyze polymerization (Table 4). Because of the dynamic nature of the flame test, these two metrics (char length and char yield) must be examined together in order to determine performance level of a given coating. This specific solution composition excels in both areas, indicating its suitability as a FR coating on cotton fabrics.

With the ideal AMPS/MBAm composition determined, the combination of AMPS polymer with an ionic liquid was tested. Results (Table 5) indicated that while layer by layer deposition of polymer and ionic liquid coatings produce better properties than combining the two in one solution, the final coatings are not as effective as the polymer solution on its own. This can be attributed, perhaps, to the ionic liquid interfering with the formation of a polymeric network, thus reducing its ability resist flame. The presence of the ionic liquid does provide a smoother and more flexible fabric after coating, but performance was not satisfactory for these coatings.

Disclosure provides a flame retardant fabric product having a fabric, a flame retardant ionic liquid represented by Formula 3, and a binder. About 1% to about 60% by weight of the flame retardant fabric product is made up of the flame retardant ionic liquid. The fabric can be Cotton, Cellulose, Rayon, Nylon, Polyester, Polyurethane Polyamide, and Aramid.

Disclosure provides a method of preparing the flame retardant fabric. The method includes coating the fabric with the flame retardant ionic liquid represented by Formula 3 and the binder to obtain a coated fabric. The coated fabric is cured at a temperature of about 20 degree C. to about 300 degree C. for about 1 minute to about 12 hours to obtain the flame retardant fabric.

AMPS Coating on NYCO Fabric

50 Nylon 50 Cotton Universal ripstop fabric class 6 MIL-DTL-44436B pure finish (NYCO) fabric was coated with AMPS. The AMPS FR formulation optimized for cotton fabric was used in coating NYCO fabric. Vertical flame test was conducted on AMPS-coated NYCO fabric. AMPS-coated NYCO fabrics performed poorly under vertical flame testing. This result was unexpected because AMPS coated cotton fabrics exhibited excellent flame retardant behavior. Probably AMPS has less interaction with Nylon fibers compared to cotton fibers, Hydroxy Functionalized Phosphonium Ionic Liquids: Tributyl Hydroxyl Propyl Phosphonium Cation Containing Ionic Liquids Hydroxy propyl tributyl phosphonium bromide, here after referred as 'TBOP-Br' or as 'Formula 20' in this disclosure was synthesized by reacting tributyl phosphine, [Bu3P] with bromo propanol (Example 22). The chemical structure of 'TBOP-Br' is provided below.

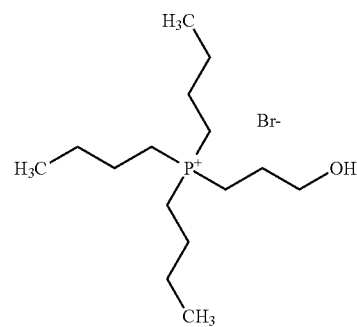 [SMILES: CCCC[P+](CCCC)(CCCC)CCCO ; [Br-]]

TBOP, when combined with urea, demonstrated excellent flame retardant property on a NYCO fabric. Vertical flame test results are provided in Table 6. Although TBOP by itself did not function well as a flame retardant coating, the combination of this liquid and urea gave results better than TPEP and EIP ionic liquids. The interaction of TBOP and urea is most likely similar to the tetrakis hydroxyl methyl phosphonium chloride salt (THPC) (commercially available under the trade name, Pyrosan®), due their similar chemical structures.

When paired with other fabric binders such as Knittex® from Huntsman, the fabric performed similarly on vertical flame testing. A combination of Titanium (IV) oxide and TEOS added to the TBOP/urea mixture provided results similar to those of pure TBOP/urea, although the fabric had a white tint from the $TiO_2$ powder.

Thermogravimetric analysis (TGA) can be helpful in deducing the decomposition mechanism of flame retardant coated fabric. Therefore, the thermal degradation behaviors of uncoated NYCO (control) and TBOP/Urea coated NYCO fabrics were analyzed using TGA. High thermal stability of TBOP ionic liquid is clearly demonstrated by the TGA curve provided in FIG. 15. The initial decomposition temperature of TBOP is about 290 degree C. Thermal decomposition of NYCO fabric in air occurs in two stages. The first stage decomposing temperature of uncoated-NYCO fabric is 342 degree C. corresponds to the decomposition of cotton in the NYCO fabric. This decomposition temperature is shifted to 311 degree C. by the phosphonium catalyzed decomposition of cotton. This behavior is similar to the behavior of THPC flame retardant material. But the initial decomposition temperature of THPC is around 184 degree C. compared to 311 degree C. for TBOP indicating the relatively higher thermal stability of TBOP. The second stage weight loss is centered around 446 degree C. is due to the decomposition of Nylon material in the NYCO fabric. This decomposition temperature is also decreased in the TBOP-Br/Urea coated NYCO fabric. This indicates that hydroxyl or amine functionalized phosphonium ionic liquids interact with both cotton and nylon fibers of the NYCO fabric. Therefore, hydroxyl or amine functionalized phosphonium ionic liquids can be used as FR coating on both 100 percent cotton fabric and 100 percent nylon fabric. The residue from sample TBOP-Br/Urea coated fabric was a rigid black solid with the original sample form and fabric weave patterns visible. The residue from uncoated NYCO fabric was a fluffy white solid. These observations clearly demonstrate the efficient char formation in the case of phosphonium ionic liquid coated samples supporting the observations made during the vertical flame testing.

Amino Functionalized Phosphonium Ionic Liquids Tributyl Amino Propyl Phosphonium Bromide (TBAP-Br)

Amino propyl tributyl phosphonium bromide, here after referred as 'TBAP-Br' or as 'Formula 23' was synthesized by reacting tributyl phosphine with 3-bromopropylamine hydrobromide. TBAP-Br was tested both by itself and with urea in the FR coating formulation on NYCO fabric. The combination of TBAP-Br and urea produced excellent results, with an average char length of 4.37 inches, and an average char yield of 93.1%. Pure TBAP-Br produced good data as well, with averages of 5.16 inch char length and 91.9% char yield. The vertical flame test data are provided in Table 8. The data indicate that amino functionalized phosphonium ionic liquids are suitable as FR coating materials.

Phosphorus-Nitrogen Synergism

It is a well-known fact that there exists a phosphorus-nitrogen (P—N) synergistic action in the flame retardancy of cellulosic fibers. Addition of nitrogen containing compounds, such as urea, cyanamides, dicyandiamide, guanidine salts, and melamine compounds to phosphorus compounds increase their flame retardancy, even though nitrogen containing compounds themselves do not exhibit FR property. In TBAP-Br both P and N present in the same molecule. In this way TBAP-Br is analogous to [TBOP-Br+Urea] formulation. The presence of the amino group on TBAP-Br already gives it a potential edge over TBOP-Br because it may not require additional nitrogen additives. Without wishing to be bound by theory, it is thought that the mechanism of P—N synergistic action is acting on the FR property of TBAP-Br and TBOP-Br ionic liquids.

In order to farther established the use of hydroxyl or amino functional groups on the ionic liquids, a compound (Tetrabutyl phosphonium bromide) which has chemical structure similar to TBOP and TBAP were tested to evaluate how critical is presence of the hydroxyl or amino group in the phosphonium ionic liquid for imparting FR property to the fabric. The Tetrabutyl phosphonium bromide and Tetrabutyl phosphonium bromide mixed with urea solutions produced average char lengths of 8.2 and 7.1 inches respectively. These values are quite high relative to results of TBAP-Br and [TBOP-Br]+Urea vertical flame test results, and three of the six samples tested did char completely. Char yield values were 64.6 percent for Tetrabutyl phosphonium bromide and 75.2 percent for Tetrabutyl phosphonium bromide mixed with urea, both significantly lower than the percentages achieved with TBAP-Br which was greater than 90 percent. This data establish that presence of hydroxyl or amino functional groups is important for flame retardant performance of the phosphonium ionic liquids.

Reviews of commonly used flame retardants have shown that halogen containing coatings may have environmental or other health risks associated with them. Bromine compounds, in particular, are under a great deal of scrutiny, with risks of bio accumulated toxic exposure during processing [R. Horrocks, Flame retardant challenges for textiles and fibers: New chemistry versus innovatory solutions, *Polymer Degredation and Stability*, 96, 377-392 (2011)]. TBAP and TBOP both have a bromide as the anion, but it can be replaced by a number of safer alternatives as provided in FIG. 1, each with a unique contribution to the compound's properties. Three common anions were exchanged with the bromide ion on TBAP-Br to demonstrate the possibility of producing bromine-free flame retardant ionic liquids based on TBAP cation.

Tributyl-Propyl Amino Phosphonium Dibutylphosphate (TBAP-DBP)

Tributyl-Propyl Amino Phosphonium Acetate (TBAP-Acetate)

Figure 21:
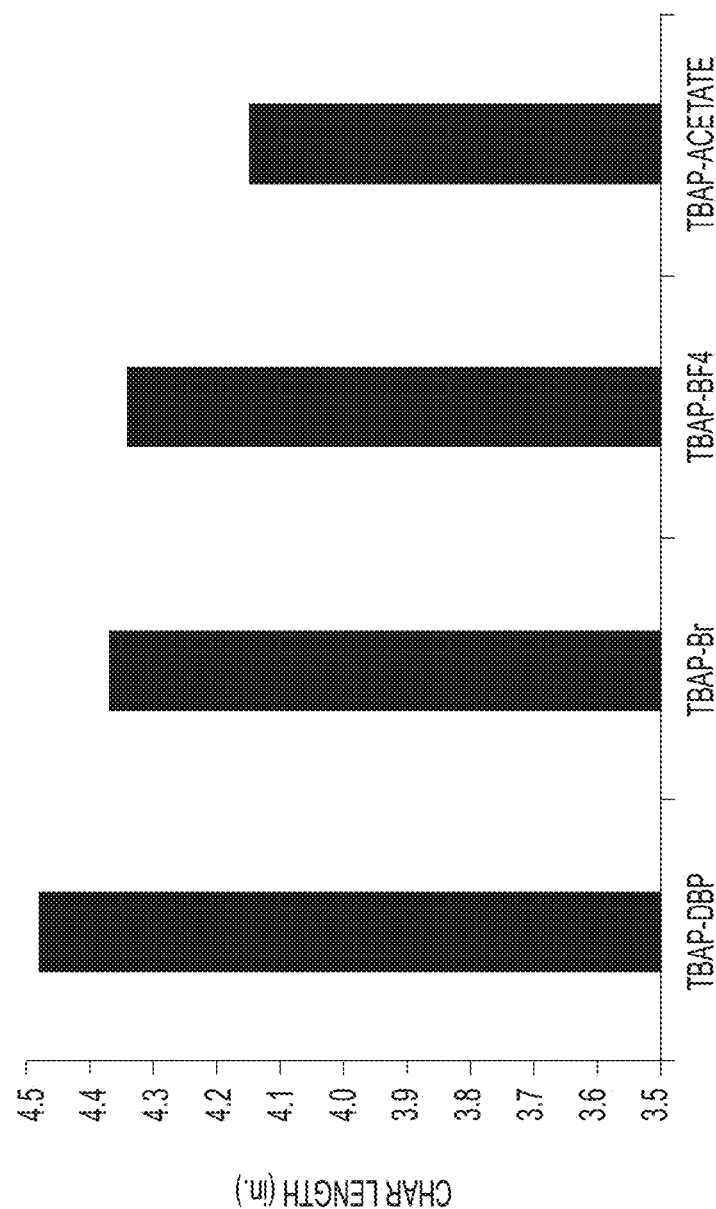

The vertical flame test data of acetate anion is compared with other anions of TBAP in FIG. 21. All the TBAP-based ionic liquids tested exhibited excellent flame retardant properties with the average char length <4.5 in. indicating that the major influence on flame retardant property is due to TBAP cation. Among various TBAP-based ionic liquids tested, TBAP-Acetate exhibited lowest char length of 4.1 in. This could be attributed to lower molecular weight of acetate anion and rationalized as follows: With the equivalent coating weight increase (~35%) in all the TBAP ionic liquids, the concentration of TBAP cation is maximum in the case of TBAP-acetate. Because the TBAP cation is the major contributor to the flame retardant property, TBAP-Acetate exhibits the best FR property among the TBAP ionic liquids tested.

Binder Systems

The durability of the FR coating is one of the most important aspects of the application. However, while effective binding systems for cotton fabrics are common, the low reactivity of nylon has made imparting a durable FR coating to NYCO fabrics a difficult task. Binding agents for fabrics can consist of polymers such as polyurethane, polyvinyl chloride, polyacrylate, or use nitrogen containing compounds including but not limited to melamine and urea to link coating molecules to the fabric and create a network that does not wash off easily. There are two possible methods of adhering the ionic liquid to the fabric. The first is a reaction mechanism that bonds the ionic liquid molecule to the fabric directly, either by some type of activation or the presence of a catalyst. The second possible route is to react ionic liquid with another compound or set of compounds that then bonds to the fabric. A polymeric network of FR compound interlaced within a binding material is a common method for imparting a durable coating to fabrics.

Samples were washed thoroughly with cold water by hand, rinsing the fabric completely to ensure that any washable coating was removed. The AATCC outlines the procedure for commercial washing [Standard Laboratory Practice for Home Laundering Fabrics Prior to Flammability Testing to Differentiate Between durable and Non-Durable Finishes, AATCC Monograph, M7, (1991)].

Dimethylol dihydroxyethyleneurea (DMDHEU) and Dimethylol ethyleneurea (DMEU) are two common finishing agents that can be used as binders. However, they are primarily used with cellulosic fabrics. A commercial product Knittex® 7636 (primary ingredient DMDHEU) was tested with a TBAP-Br coating of the NYCO fabric, but less than 20% of the coating applied was retained after just one wash.

In order to determine the potential utility of a binding agent, product samples were tested initially with a solution containing only the binder. If a high amount of the binder coating (>85%) was retained after washing, it was then tested with ionic liquid systems. Lubrizol produces a variety of finishing applications for textiles, and three products from the company were tested: PrintRite® 595, an acrylic binder, Vycar® 580X182, a PVC dispersion, and Sancure® 20025F, a polyurethane mixture. Two other acrylic binders from Huntsman Chemical were also tested: Dicrylan® AC-01 and Dicrylan® TA-GP. Finally, a binding system composed of a melamine-formaldehyde finishing agent and a urea based cross linker from Emerald Performance Materials were tested. The components are Aerotex® resins, entitled M3, 3730, and 3030.

Varying the amount of the binder often resulted in different retention values, most likely due to compounds' ability to interact with the fabric in the presence of water. If a given composition of binder was not durable, alternate compositions were tested until a successful composition was found or the material was deemed unusable as a binding agent.

The acrylic binders (PrintRite/Dicrylans) provided some retention of the coating, with PrintRite adhering best to the fabric. However, the lack of nitrogen in the compound makes it difficult to impart complete FR properties to the fabric. Sancure showed very high retention by itself, but formed a separate phase when placed into solution with TBAP-Br. Its inability to mix in water with TBAP compounds made it unusable for further tests. Polyurethanes react well with hydroxyl groups, which are abundant on the NYCO fabric. The best binding system for amine and hydroxyl functionalized phosphoinium-based ionic liquids determined to be melamine based binder products including but not limited to Aerotex M3 resins available from Lubrizol along with cross linkers including but not limited to acrylates, aerotex 3030 and aerotex 3730.

Antielectrostatic Property

In general, textile fabrics are electric insulators with surface resistance in the range of 1013 Ω to 106 Ω [P. J. Žilinskas, T. Lozovski, V. Jankauskas, J. Jurksus, Electrostatic Properties and Characterization of Textile Materials Affected by Ion Flux, MATERIALS SCIENCE (MEDŽAGOTYRA) 19, 201 (2013)]. Surfaces with high electrical resistance are susceptible for electrostatic charging. An accumulated electric charge has the ability to generate and retain an electrostatic field of significant magnitude. This electric field can be detected as a surface voltage that can be measured. Thus the surface voltage can be a measure of the electrostatic properties of the test fabric.

Ionic liquids consist of charged species with high ionic conductivity. The static charge accumulated on the fabric surface can be rapidly dissipated by conducting ions. Antistatic property of the TBOP-Br/Urea treated fabrics were tested using the Federal Test Method Standard 191A Method 5931 'Determination of electrostatic decay of fabrics'. According to this method the amount of time it takes for static to dissipate from a fabric strip was measured. The 3"×5" test samples were pre-conditioned at 20% relative humidity at 24° C. 5000 V was applied to the test fabric for a period of 20 seconds. The voltage behavior of the test sample as a function of decay time was recorded. The time for the charge to decay from the maximum voltage level to 50% of the maximum voltage attained was measured from the voltage decay plot. The decay time for the uncoated and TBOP/Urea coated fabrics were provided in Table 6. The electric charge applied on to the TBOP/Urea coated fabric was rapidly removed compared to uncoated NYCO fabric.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

Synthesis of [Hydroxy Propyl Methyl]-imidazolium Bromide, [OHpmim]Br

Methyl imidazole (0.063 mol, 5 mL) was mixed with 3-bromopropanol (0.095 mol, 13.2 g) in a round bottom (RB) flask. The mixture was heated to 80 degree C. with a reflux condenser. The reaction continued for 24 h. After the reaction, the top layer was decanted off. The product was washed with diethyl ether (5 mL 3×) and dried under vacuum at 80 degree C. for 2 days and analyzed with proton nuclear magnetic resonance spectroscopy (NMR). Proton NMR Data: 8.866 (s, 1H, aromatic), 7.609 (s, 1H, aromatic), 7.547 (s, 1H, aromatic), 4.377 (t, 2H), 3.976 (s, 3H-Ring CH3), 3.675 (t, 2H, —N—CH2), 3.592 (t, 2H, —CH2-OH), 2.172 (m, 2H)

Example 2

Synthesis of Hydroxybutyl Methyl Imidazolium Chloride 15 mL of 4-cholorobutanol (1.5 mol) was mixed with 7.98 mL of 1-methyl imidazole and stirred at 80 deg C. with reflux condenser. The reaction was continued for 24 h then cooled to room temperature. The excess unreacted 4-cholorbutanol was removed by washing with diethyl ether (5 mL, 3×). Then the sample was dried at 80° C. under reduced pressure. Proton NMR Data: 8.856 (s, 1H, aromatic), 7.606

(s, 1H, aromatic), 7.583 (s, 1H, aromatic), 4.364 (t, 2H), 4.364 (2H—CH2-OH), 4.032 (s, 3H-Ring CH3), 3.703 (t, 2H, —N—CH2), 2.034 (t, 2H, —CH2-OH), 1.676 (m, 2H). Corresponding compounds with ethyl imidazole also prepared with 3-bromopropanol and 4-chlorobutanol.

Example 3

Synthesis of [Amino propyl methyl]-imidazolium bromide [apmim]Br 102 g of 3-bromopropylamine hydrobromide (0.456 mol) was dissolved in dry ethanol. To this solution 1-methylimidazole (36.4 mL, 0.456 mol) was added. The mixture was stirred for 24 h at 80 deg C. White solid was formed was recrystallized from ethanol. Proton NMR Data: 8.842 (s, 1H, aromatic), 7.580 (s, 1H, aromatic), 7.505 (s, 1H, aromatic), 4.378 (t, 2H), 3.932 (s, 3H-Ring CH3), 3.103 (t, 2H, —N—CH2), 2.320 (t, 2H, —CH2-OH), 2.074 (t, 2H)

Example 4

Ion-Exchange with Lithium Bis(trifluoromethylsulfonyl) Imide Anion

Ionic liquids containing anions other than bromide ion can be prepared by ion-exchanging the bromocompound with alkali salts of other anions. For example, ionic liquids with Bis(trifluoromethyl sulfonyl) imide anion can be prepared by ion-exchanging the bromide compound with Lithium Bis(trifluoromethyl sulfonyl) imide (LiNTfsub.2). 11.28 g of LiNTfsub.2 was dissolved in 50 mL acetone. Then 5 g of [hydrxypropyl-methyl imidazolium]bromide was added to the Bis (trifluoromethylsulfonyl) imide anion solution and stirred in a 200 mL round bottom flask for 24 h. Then 200 mL of deionized water was added to dissolve LiBr. Hydrophobic ionic liquid layer settled at the bottom. The solution was decanted to isolate the ionic liquid compound with NTfsub.2 anion. Similarly, amino compound also ion-exchanged with LiNTfsub.2 to form the corresponding ionic liquid. Amine- and hydroxyl groups containing ionic liquids when mixed with each other consistently showed higher carbon dioxide absorption capacity compared to the corresponding compounds alone.

The following examples are focused on preparing new ionic liquids in which both amino and alcohol groups will be present in the same molecule. Interestingly recent research reports showed that mixing super bases with alcohol containing ionic liquids were found to be effective for equimolar carbon dioxide capture under ambient pressures [C. Wang, H. Luo, X. Luo, H. Li, and S. Dai, Equimolar CO2 capture by imidazolium-based ionic liquids and superbase systems, Green Chem. 12, 2019-2023 (2010)]. However, this systems seems to have low recyclability.

Example 5

Synthesis of Ionic Liquid Represented by the Formula 8

Formula 8

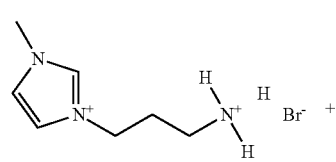

-continued

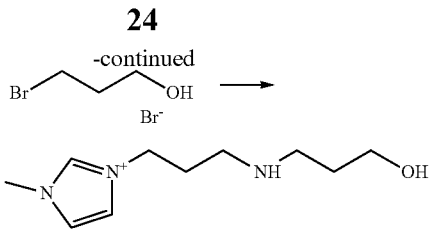

Figure 3:
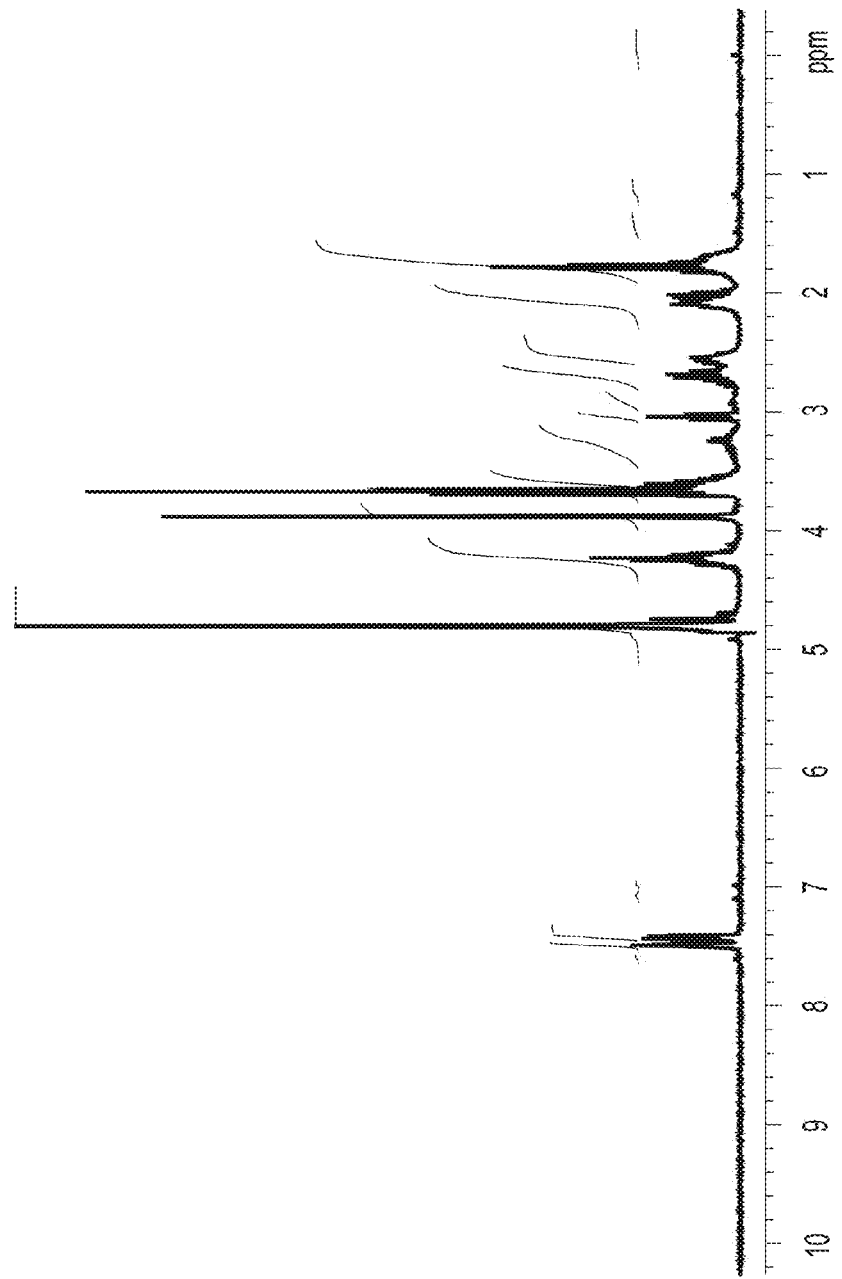
FIG. 3. Proton nmr spectrum of Formula 8
Figure 4:
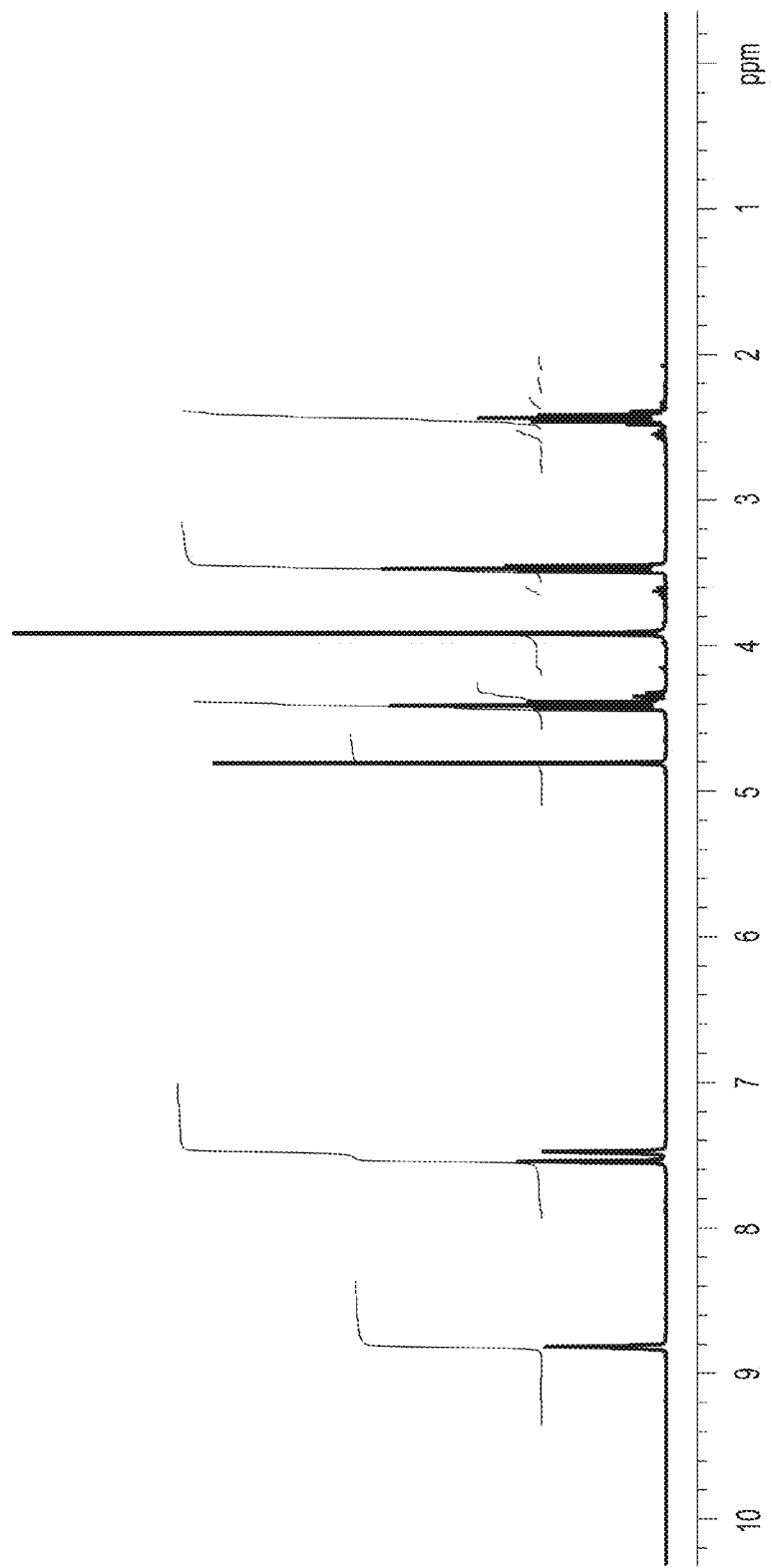
FIG. 4. Proton nmr spectrum of Formula 9

In a typical reaction, 3 g of aminopropyl-methyl imidazolium bromide was dissolved in ethanol. 6.9 g potassium carbonate and 4.14 g of bromopropyl alcohol were added to this solution and reacted at 50 degree C. for 12 h. After the reaction the solvent was removed by rotoevaporation. The solid was extracted with ether to remove unreacted bromopropyl alcohol. The proton nmr of the product is provided in FIG. 3. The proton nmr distinctly different from the starting material showing that the reaction has proceeded to completion. However, proton correspond to C-2 in the imidazolium ring was not observed in the nmr spectrum. This reaction was repeated several times with various conditions including different solvent, temperatures, and molar ratio of the reactants. In all the variations that we tried the resulting product was similar and did not show C-2 hydrogen. Since, the expected product was not obtained, we tried an alternative approach to synthesize amino-alcohol groups containing imidazolium compounds.

Example 6

Synthesis of [bromopropyl-methyl]imidazolium Bromide

In the alternative method bromoalkyl imidazolium compound was first synthesized. Then this intermediate compound was reacted with various alkanol amine compounds to form the corresponding ionic liquids as bromide salts. The reaction scheme for the synthesis of bromopropyl-methyl imidazolium bromide is provided below:

Formula 9

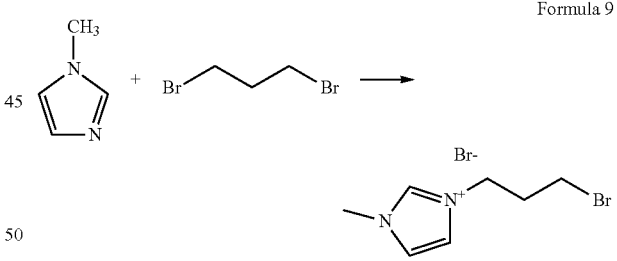

Figure 7:
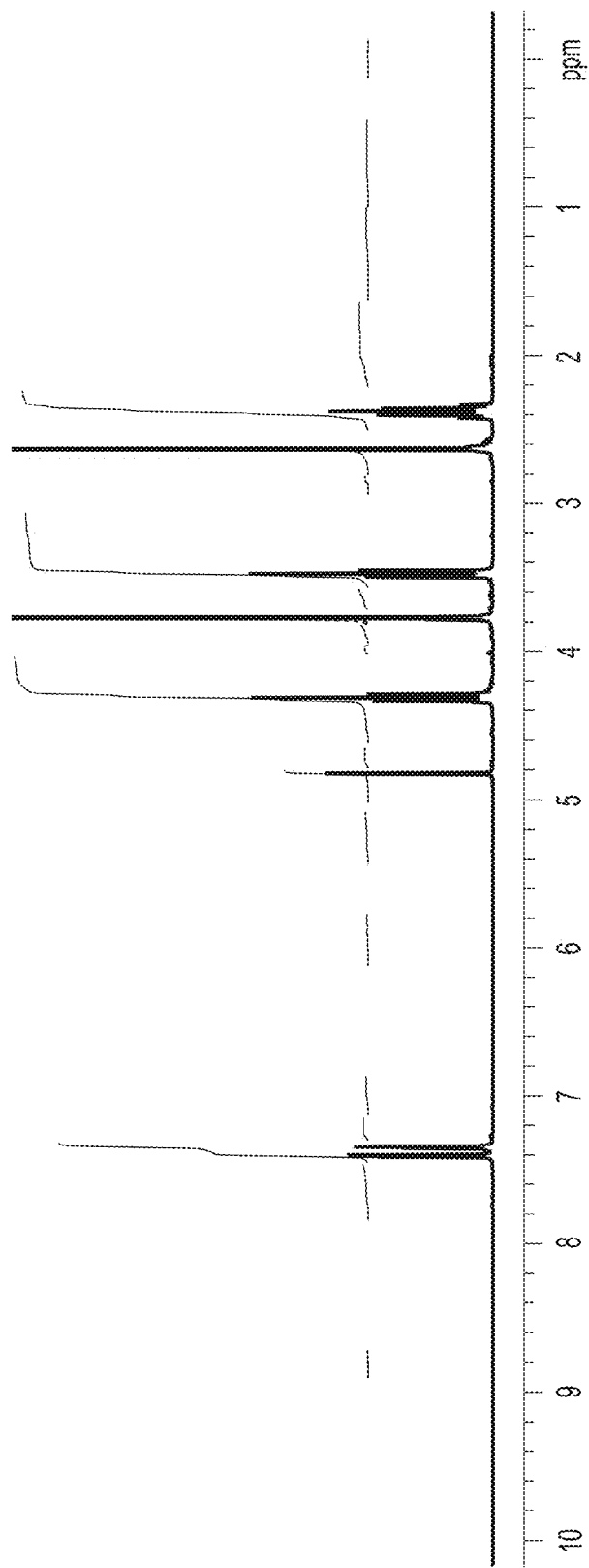
FIG. 7. Proton nmr spectrum of Formula 11 (Bromopropyl-dimethyl imidazolium bromide)

In a typical reaction, 28.5 g (0.134 mol) of 1-methyl imidazole was taken with 55 g (0.201 mol) of 1,3-dibromopropane (1:1.5 ratio) in acetonitrile solvent. The mixture was heated to 50 deg C. In 3-5 min of addition of methyl imidazole to dibromopropane, a cloudy solution was formed. The internal temperature was raised to 70 deg C. during the further addition of imidazole. The addition of methyl imidazole in acetronitrile was controlled such that the reaction mixture temperature remains constant around 55 deg C. After completion of the addition of methyl imidazole the reaction mixture was cooled to room temperature. The reaction mixture was rotoevaporated to remove the solvent. Then the white solid formed was washed with diethyl ether to remove the excess dibromopropane. The dried product contained both monomer and dimers. The required monomer product compound 4 was separated by dissolving in acetonitrile. The proton nmr of the monomer compound bromopropyl methyl imidazolium bromide is provided in FIG. 7. The reaction was conducted at various temperatures between 40 to 55 degree C. The monomer yield in the final product was increased with increase in temperature. Further, diluting the reactants in acetonitrile also helped in increasing the monomer yield. Proton NMR Data in D2O: chemical shift 8.82 (s, 1H), 7.55 (d, 1H), 7.47 (d, 1H), 4.41 (t, 2H), 3.92 (s, 3H), 3.47 (t, 2H), 2.44 (2H).

Example 7

Reaction of Bromopropyl-Methyl-Imidazolium Bromide with Alkanol Amines

Bromoalkyl methyl imidazolium bromide can be reacted with a variety of aminoalkanol compounds forming the corresponding ionic liquid. For example, ionic liquid represented by the Formula 10 was synthesized by reacting bromopropyl methyl imidazolium bromide (Formula 9) with N-methyl ethanolamine in the presence of potassium carbonate is provided below.

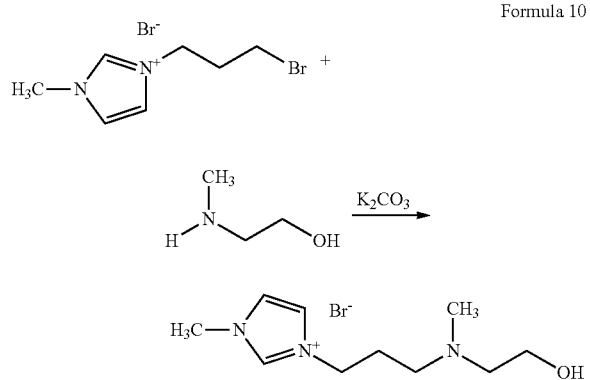

Formula 10

Figure 5:
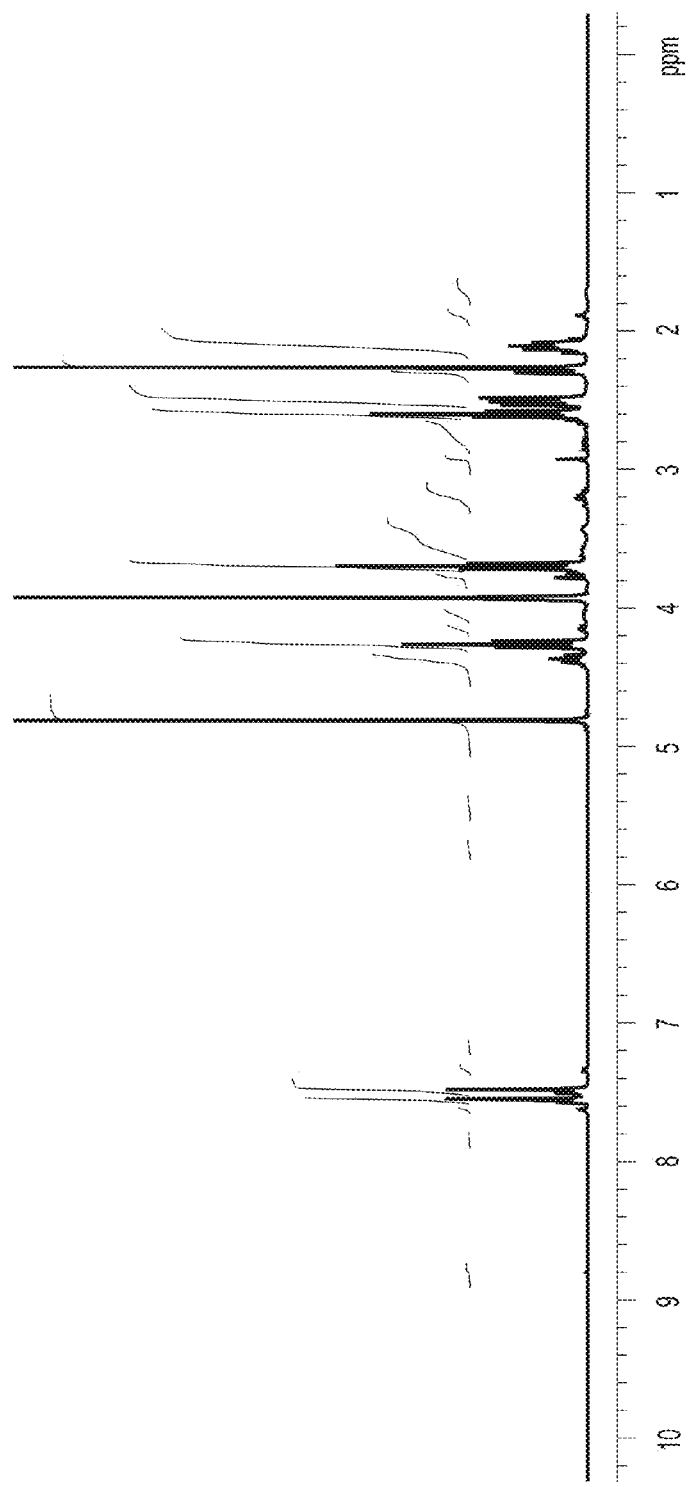
FIG. 5. Proton nmr spectrum of Formula 10, the product from the reaction between bromopropyl-methyl imidazole and N-methyl ethanolamine.

In a typical reaction, 6 g (0.02 mol) of bromopropyl-methyl imidazole, 1.58 g (0.02 mol) of N-methyl ethanolamine and 5.83 g of potassium carbonate 0.04 mol) were mixed in 30 mL of acetonitrile and heated at 65 deg C. for 1 h. After the reaction the solid was filtered off and washed with acetonitrile. The filtrate was rotoevaporated to remove the solvent. Then extracted with tetrahydrofuran (THF) in which N-methyl amino ethanol is soluble. Then the sample is dried under high vacuum. The proton NMR spectrum of the dried product is provided in FIG. 5.

Figure 6:
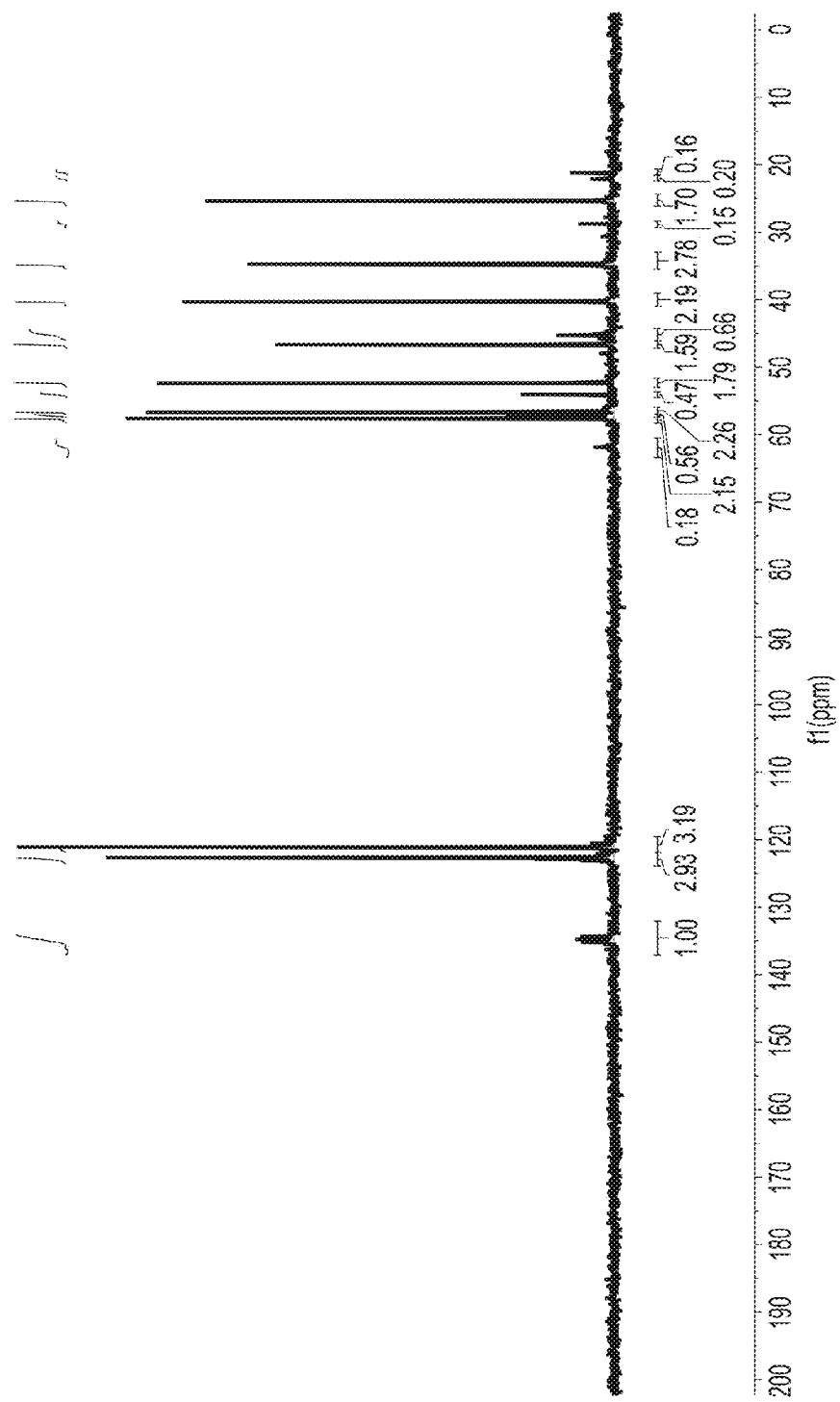
FIG. 6. C-13 NMR spectrum of Formula 10

NMR Data: proton NMR in D2O Chemical shift 7.52 (d, 1H), 7.47 (d, 1H), 4.23 (t, 2H), 3.89 (s, 3H), 3.69 (t, 2H), 2.58 (t, 2H), 2.51 (t, 2H), 2.25 (s, 3H), 2.08 (m, 2H). This structure was further supported by C-13 NMR spectrum of the ionic liquid represented by the Formula 10 provided in FIG. 6. C-13 NMR Data: 122.7 (CH), 121.3 (CH), 57.5 (CH3), 56.8 (CH2), 52.5 (CH2), 46.7 (CH2) 40.2 (CH3), 34.5 (CH3), 25.2 (CH2)

Example 8

Synthesis of bromopropyl dimethyl-imidazolium bromide was achieved according to the reaction scheme below:

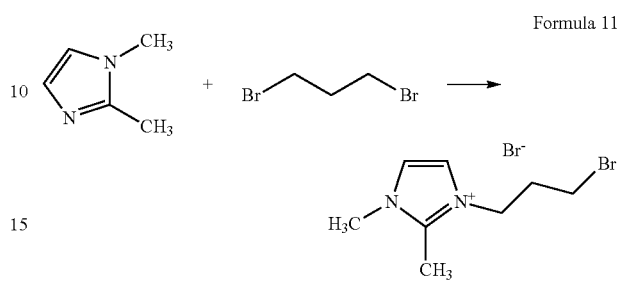

Formula 11

To a solution of 1,3-dibromopropane (126.02 g, 0.6242 mol) in 150 mL of acetonitrile a solution of 1,2 dimethyl imidazole (30 g, 0.3121 mol) was added drop wise at 80 degree C. The addition was completed in about 2 h. Then the reaction mixture was left to stir at 75 degree C. overnight. After completion of the reaction, the solvent was removed by rotoevaporation under reduced pressure. White dry solid formed was treated with diethyl ether in small batches. Ether extraction was carried out for 3 times. Then the powder was dried to remove ether. Then the dried powder was stirred with acetonitrile at room temperature to isolate monomer bromopropyl compound. The undissolved dimer was separated by filtration. The filtrate was rotoevaporated to remove the solvent and dried under high vacuum. Yield 20 g. The proton NMR of the showed highly pure monomer compound. NMR Data: Proton NMR in D2O Chemical shift 7.41 (d, 1H), 7.35 (d, 1H), 4.31 (t, 2H), 3.78 (s, 3H), 3.48 (t, 2H), 2.63 (s, 3H), 2.38 (m, 2H).

Example 9

3-Bromopropyl-1,2 dimethyl imidazolium bromide compound was reacted with a number of alkanol amines, alkyl amines, cyclic amines, aliphatic cyclic amino alcohols and compounds such as 2-amino-2-methyl-1,3-propanediol, 2-piperidineethanol, 2-piperidinemethanol, diisopropanol amine, 3-quinuclidinol, N,N-dimethylethanolamine, and 3-piperidino-1,2-propandiol and sterically hindered amines to form a variety of ionic liquids containing both alcohol groups and amino groups. N-methyl ethanolamine, monoethanol amine and diethanolamine derivatives of the compound represented by the chemical Formula 11 were synthesized high yield in the presence of potassium carbonate. A typical reaction scheme of Formula 11 with N-methyl ethanol amine is provided below.

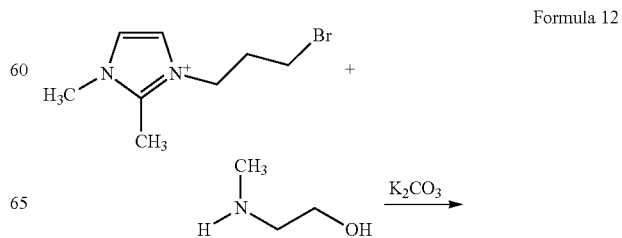

Formula 12

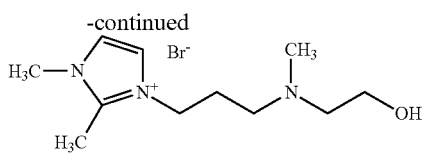

Figure 8:
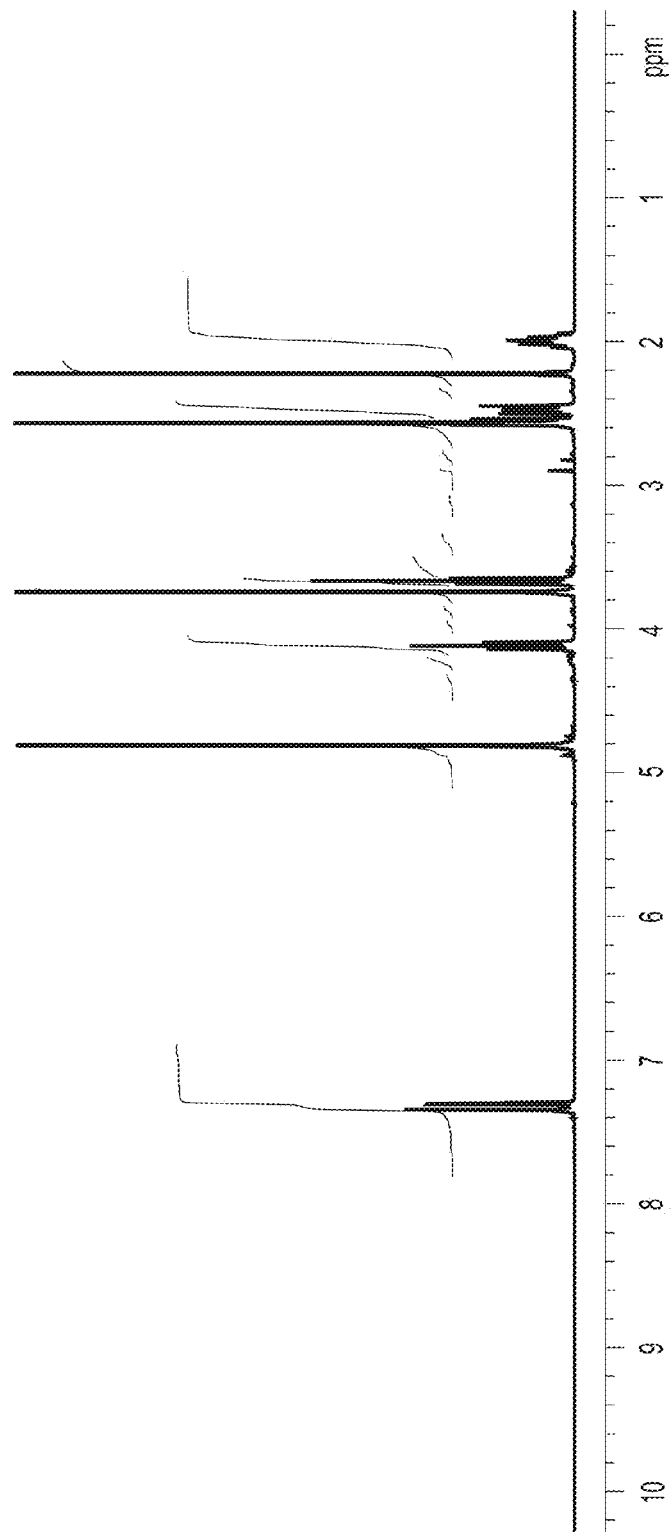
FIG. 8. Proton NMR spectrum of Formula 12
Figure 9:
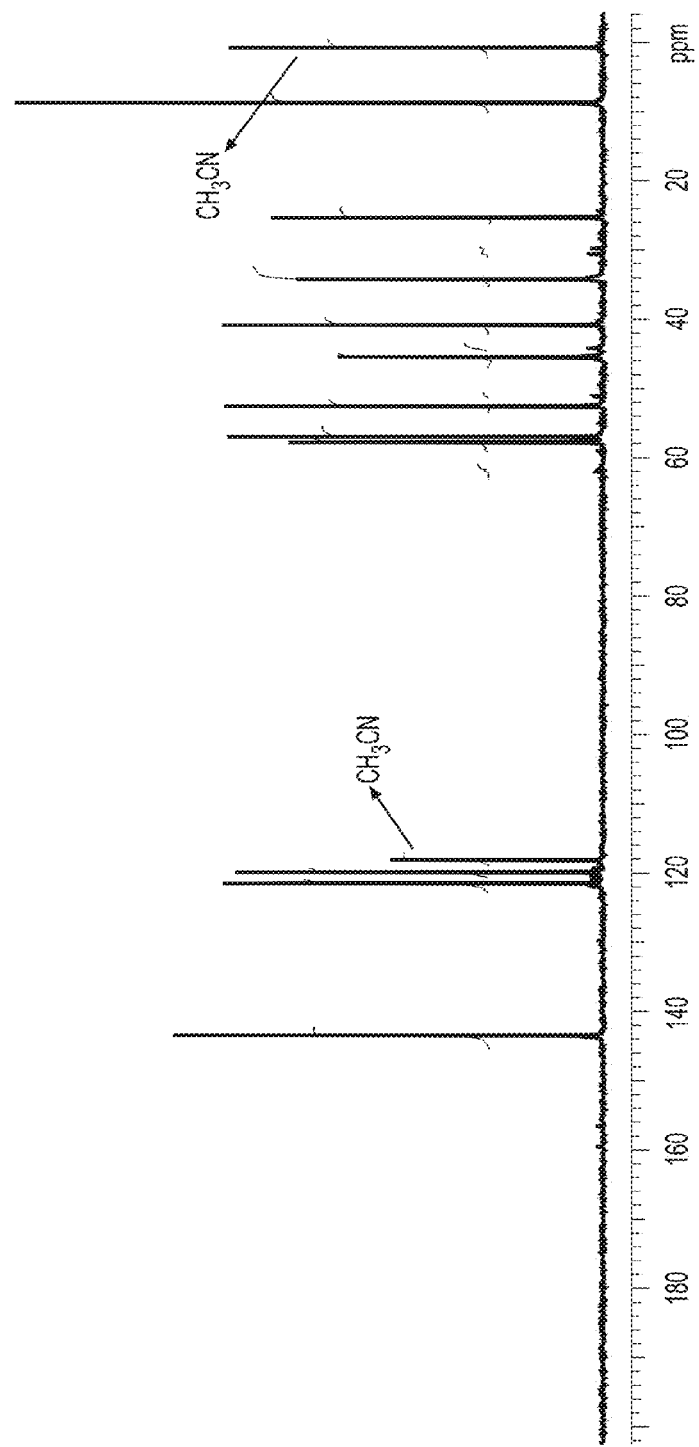
FIG. 9. C-13 NMR spectrum of Formula 12. NMR resonance peaks from acetonitrile solvent is marked in the Figure.

The proton and C-13 NMR spectra of the ionic liquid represented by the chemical Formula 12 are provided in FIGS. 8 and 9, respectively.

Proton NMR Data: Proton NMR in D2O chemical shift 7.35 (d, 1H), 7.30 (d, 1H), 4.12 (t, 2H), 3.74 (s, 3H), 3.67 (t, 2H), 2.57 (s, 3H), 2.48 (m, 2H), 2.25 (2, 3H), 1.99 (m, 2H). C-13 NMR Data: 143.4 (C), 121.5 (CH), 119.9 (CH), 57.8 (CH2), 57.1 (CH2), 52.6 (CH2), 45.5 (CH), 40.9 (CH3), 34.3 (CH3), 25.4 (CH2), 8.8 (CH3)

Example 10

Reaction of 3-Bromopropyl-1,2 dimethyl imidazolium bromide reacted with monoethanol amine resulted in the corresponding ethanol amine compound in the presence of potassium carbonate according to the reaction scheme represented below:

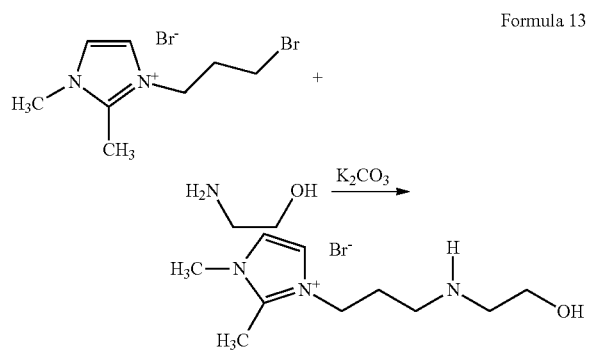

Formula 13

Figure 10:
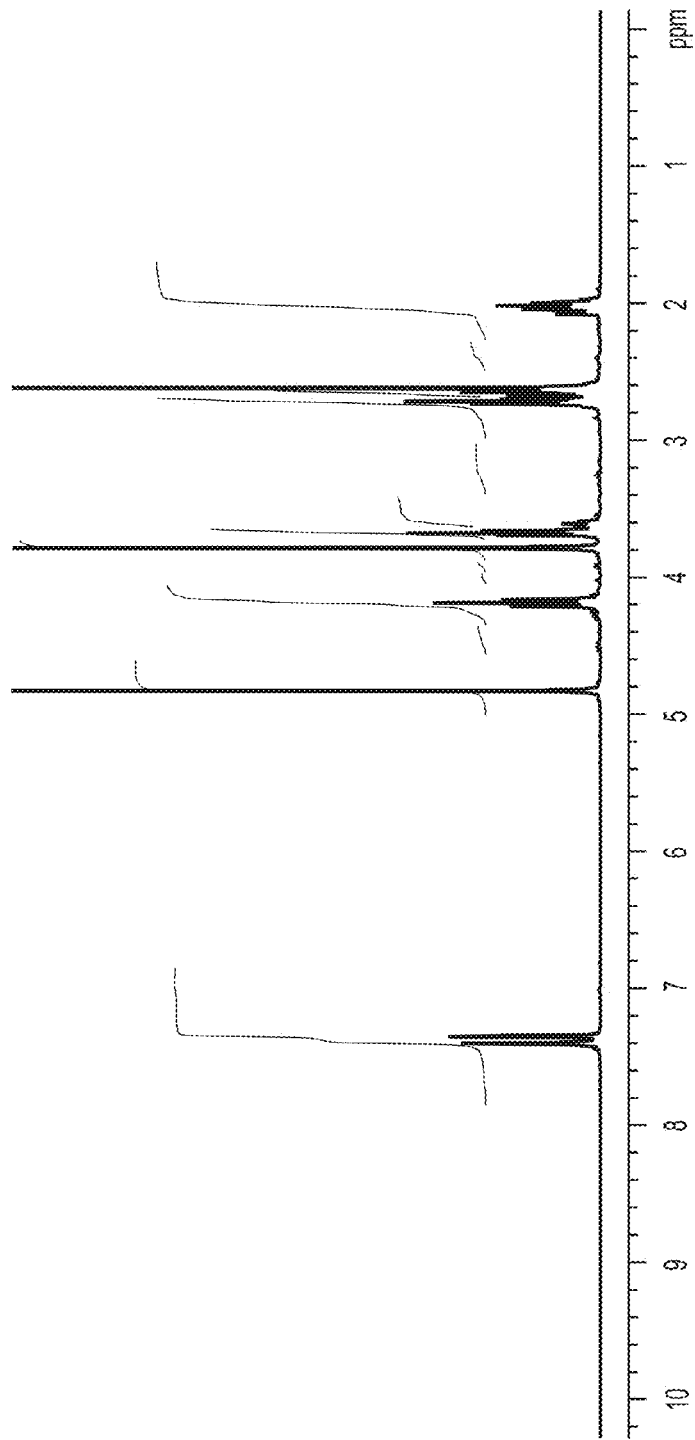
FIG. 10. Proton nmr spectrum of Formula 13
Figure 11:
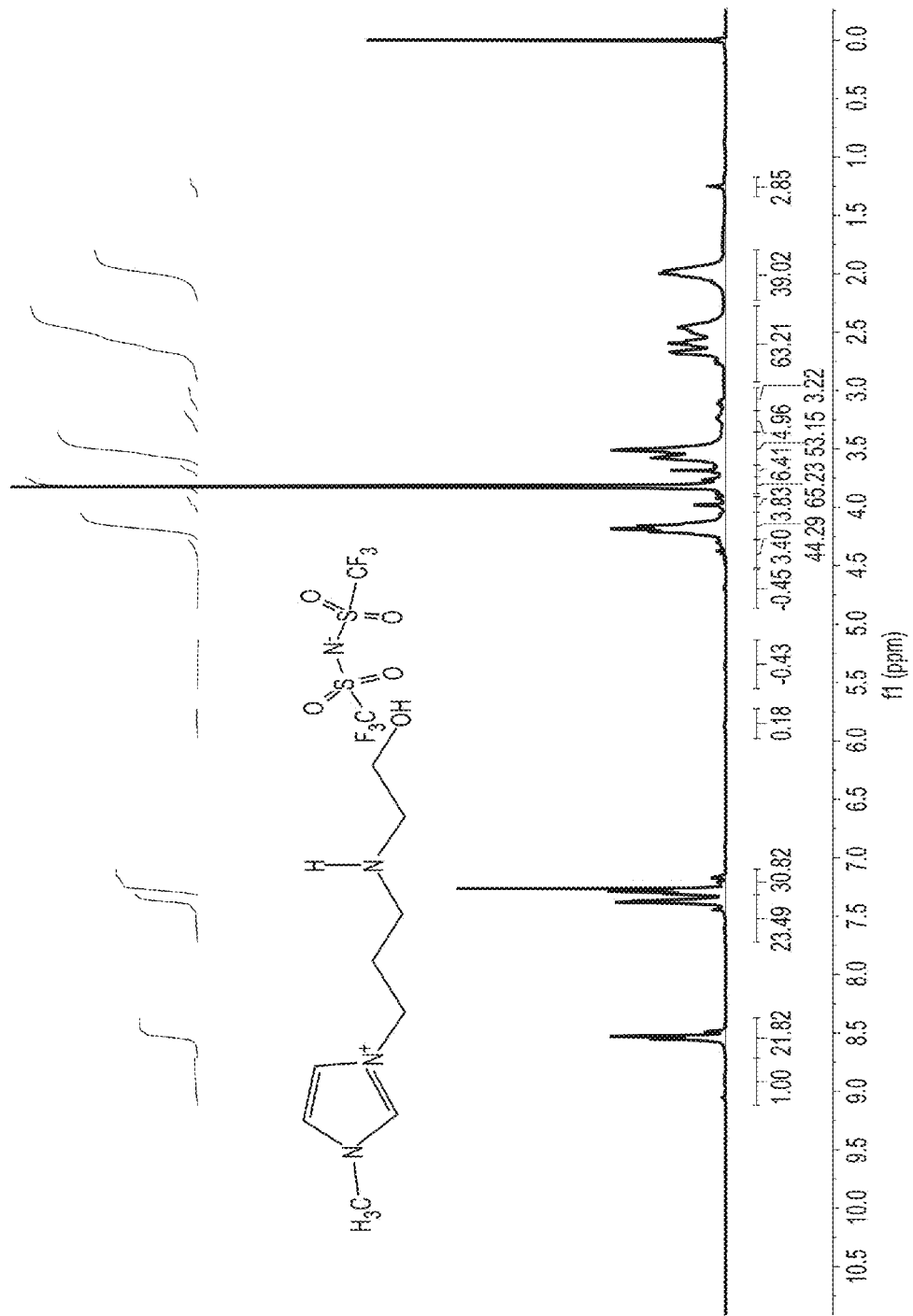
FIG. 11. Proton nmr spectrum of Formula 14
Figure 12:
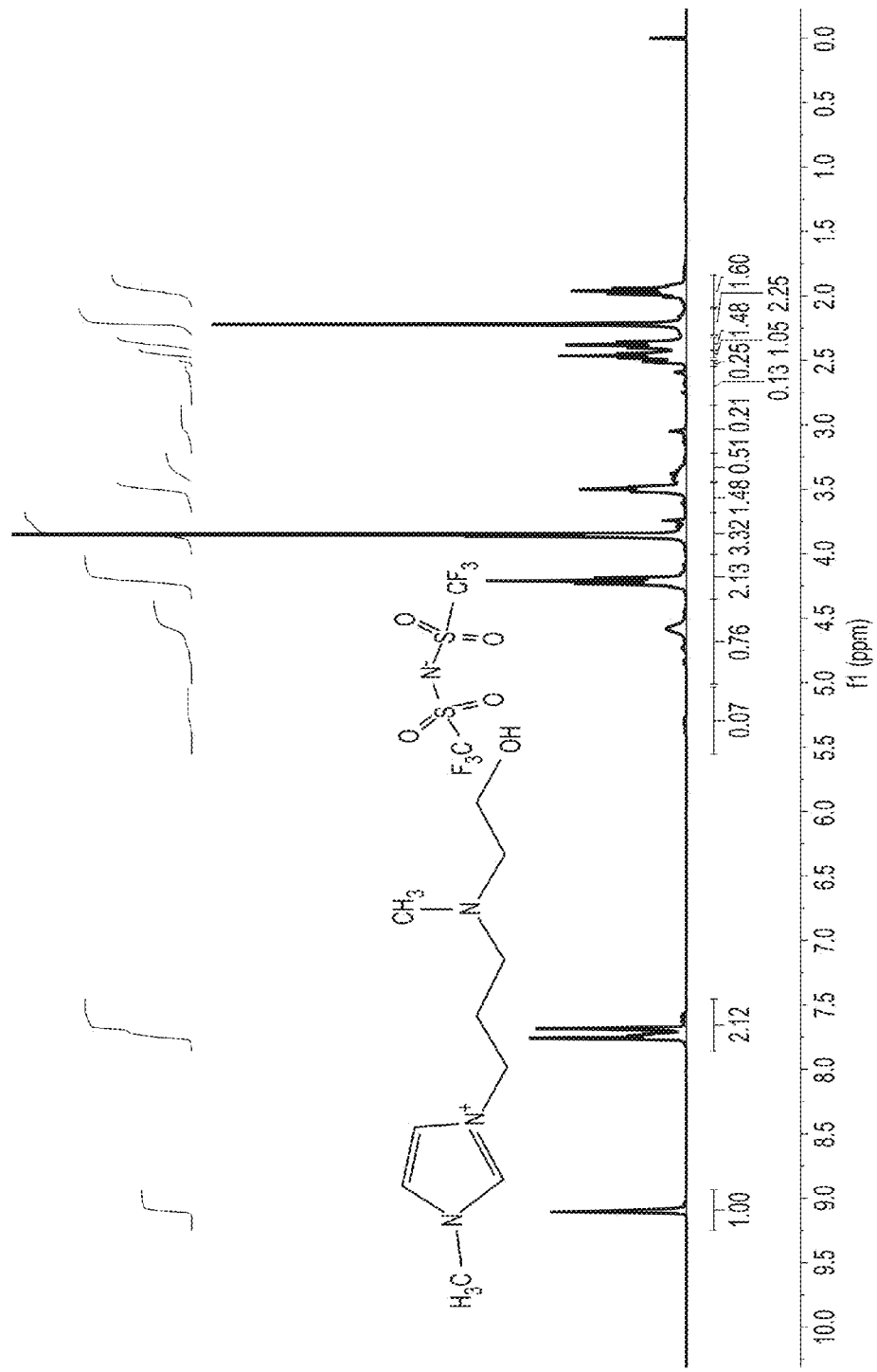
FIG. 12. Proton nmr spectrum of Formula 15
Figure 13:
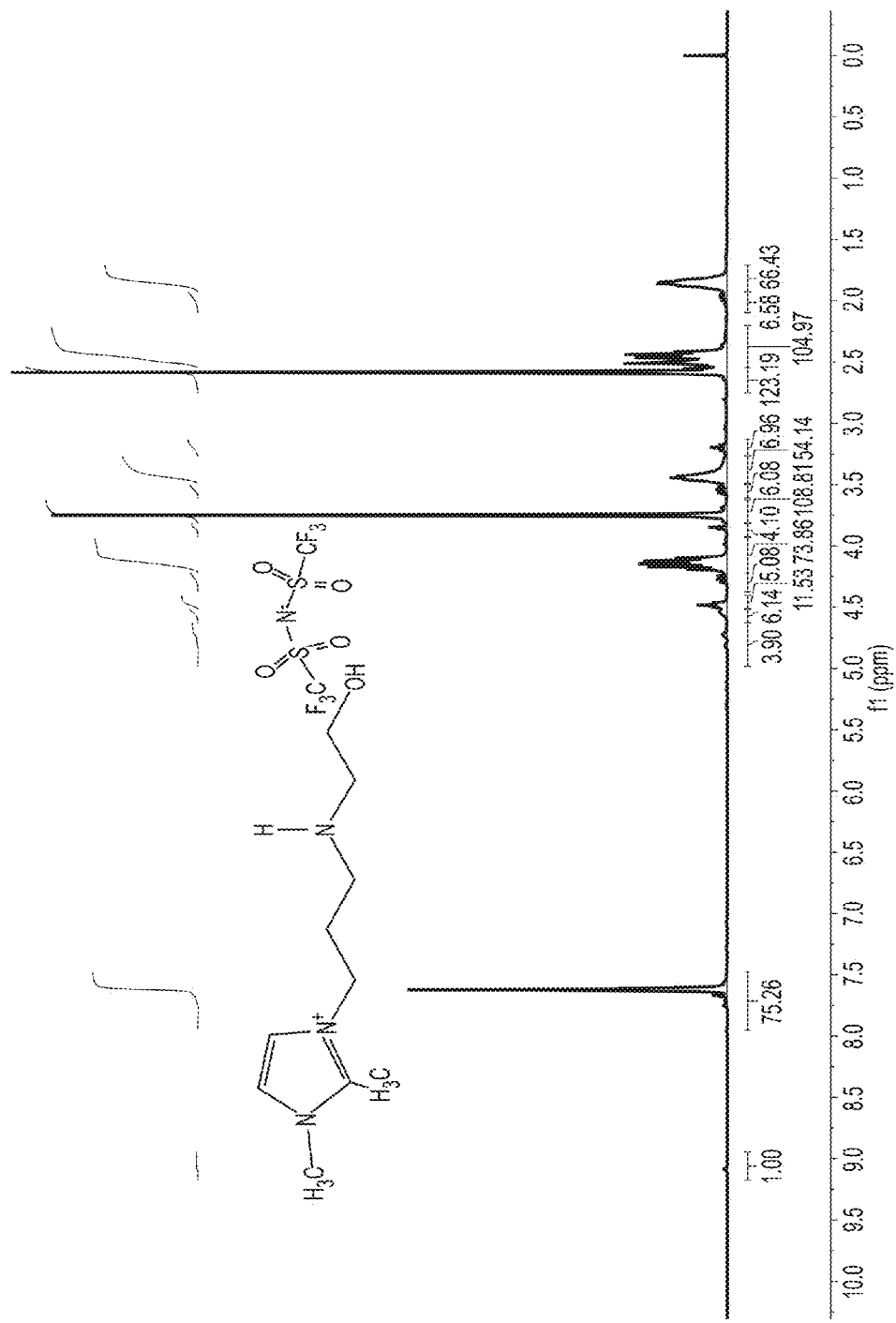
FIG. 13. Proton nmr spectrum of Formula 16
Figure 14:
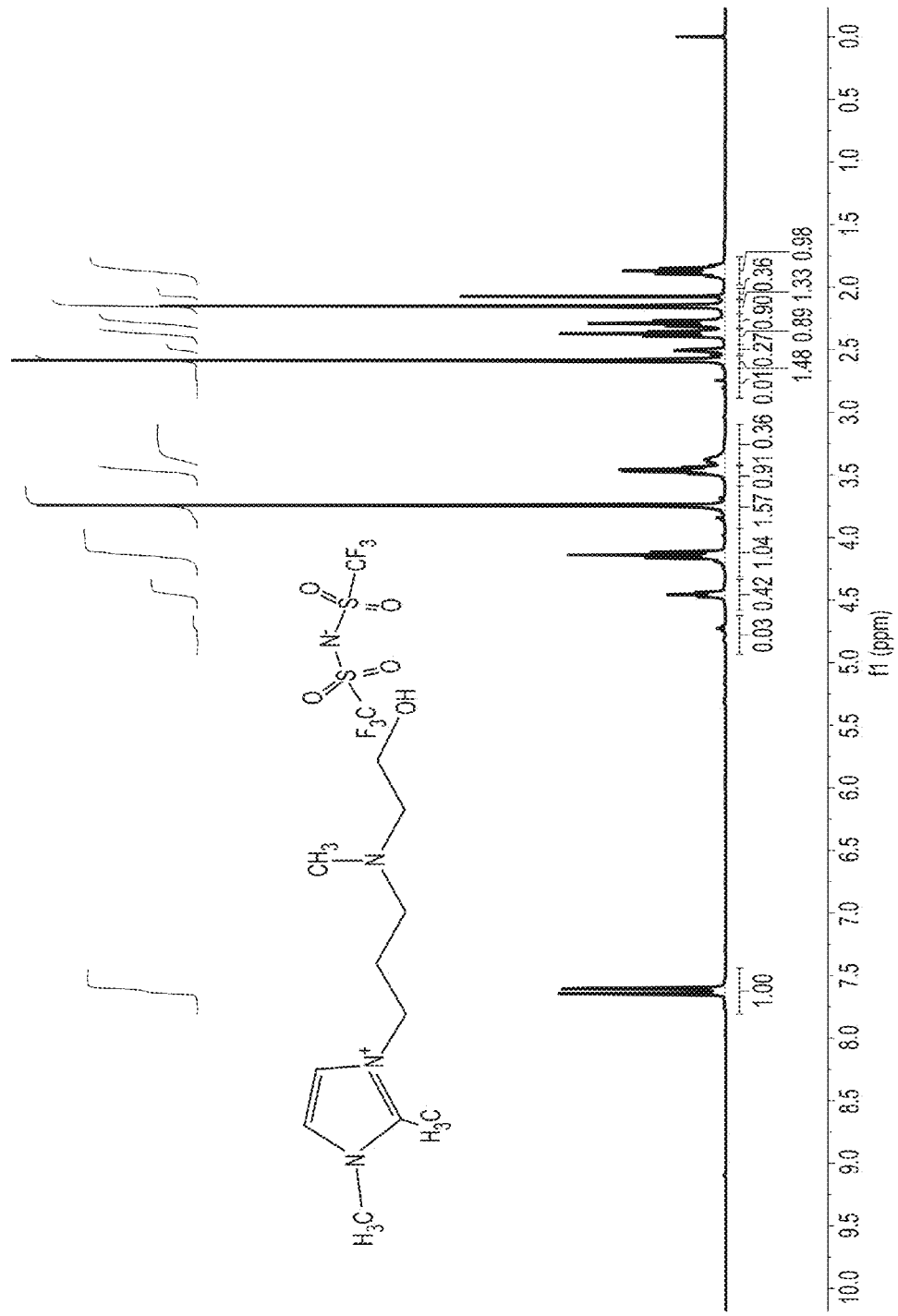
FIG. 14. Proton nmr spectrum of Formula 17

Proton NMR spectrum of the ionic liquid represented by the Formula 13 is provided in FIG. 10.

The reaction progress was demonstrated by the shift in the NMR resonance peaks for CH2-Br at 3.477 ppm shifted to CH2-N at 3.678 ppm. This clearly demonstrated the alkylation of amino groups with the bromopropyl-1,2 dimethyl imidazole.

Example 11

The compounds containing both amino and alcohol groups were ion-exchanged with Bis(trifluoromethylsulfonyl) imide anion to form the corresponding ionic liquids shown in FIG. 2. Proton NMR of the Bis(trifluoromethylsulfonyl) imide anion exchanged amino alcohol functionalized imidazolium ionic liquids are provided in FIG. 11 to FIG. 14. Similarly by ion exchanging with NaBFsub.4 resulted in corresponding ionic liquids. Other anions listed in the FIG. 1 can also be exchanged similar to Bis(trifluoromethyl sulfonyl) imide anion and BFsub.4 anion to form the corresponding ionic liquids.

Example 12

Thermal Stability of Amino Alcohol Functionalized Ionic Liquids

In order to determine the thermal stability of the functionalized ionic liquids synthesized thermogravimetric analysis (TGA) was conducted. The decomposition temperature of ionic liquids will provide data on the thermal stability of ionic liquids. The TGA was run on a TA Instruments TGA2950 (TA Instruments P/N 952250.502 S/N HA2950-R516) at Edison Analytical Laboratories, Inc., Latham, N.Y. The purge atmosphere was nitrogen at 100 ml/min. The temperature program was a ramp at 10 degree C. per minute to 600 degree C. The sample was in a platinum pan. Data collection used Thermal Advantage software v.1.1A S/N C1102272 and the analysis used Universal Analysis v. 3.4C build 3.4.0.10. The instrument was calibrated for temperature using the curie points of nickel and iron and calibrated for weight with the precision weight set provided by TA Instruments. The ionic liquid represented by the Formula 17 exhibited a larger amount of loss near 280 degree C. compared to the ionic liquid represented by the Formula 14. This can be attributed to the loss of N-methyl group. Otherwise, the two materials show similar decomposition profiles and both are completely reduced to a black char by 488 degree C.

The ionic liquids reported here show relatively lower stability than the unfunctionalized ILs reported in the literature [Z. Zhang, and R. G. Reddy, Thermal Stability of Ionic Liquids, TMS Annual Meeting held on Feb. 17-21, 2002 http://www.bama.ua.edu/zhang002/research/slideshow6.pdf]. The amino alcohol functionalized ionic liquids are stable up to 280 degree C. which is sufficiently high enough for carbon dioxide capture from flue gases and other applications. Further, it is interesting to note that the amino alcohol groups are stable up to 280 degree C., which is not possible to achieve by the physical mixing of amino alcohols or amines with an unfunctionalized ionic liquids or other solvents [D. Camper, J. Bara, D. L. Gin, R. Noble, Room-temperature ionic liquid-amine solutions: Tunable solvents for efficient and reversible capture of CO2, Ind. Eng. Chem. Res. 47, 8496-8498 (2008)). The TGA of functionalized ionic liquid represented by the chemical Formula 17 under flowing air (20% oxygen) and nitrogen and air are provided in FIG. 15. Both the curves almost overlap indicating that MMI's ionic liquids are stable in nitrogen as well as in air up to 280 degree C.

Example 13

Carbon Dioxide Absorption by Functionalized Ionic Liquids

The ionic liquid samples (about 3 g) were loaded in the isochoric cell and degassed at 80 degree C. and 3 mbar vacuum for a period of 12-18 h. After cooling the sample to 25 degree C., carbon dioxide gas was introduced into the isochoric cell. The pressure was set at desired pressure between 1-8 bar. The sample was stirred during the absorption experiment. The weight increase due to carbon dioxide absorption was measured at various exposure times. The absorption duration was kept at 18 h for all the samples uniformly. In FIG. 16, carbon dioxide absorption of functionalized ionic liquids and unfunctionalized ionic liquid hexyl methyl imidazolium Bis(trifluoromethylsulfonyl) imide (C6mimNTf2) are compared. Anions strongly organize around the amino groups forming strong hydrogen bonds. So, it may be possible to achieve high reactivity by using a different anion. Replacing H with CH3 group liberates amino group from the clutches of hydrogen bonding and helps in increasing the reactivity and absorption of carbon dioxide. Further, the amount of carbon dioxide absorption is drastically increased by the introduction of hydroxyl groups in the proximity of the amino group. The carbon dioxide absorption of C6mimNTf2 unfunctionalized ionic liquid is probably attributed to physical mechanisms, while chemical and physical mechanisms are involved in the carbon dioxide absorption of the amino alcohol functionalized ionic liquids. There are two stages of absorption observed for functionalized ionic liquids. There exists a plateau above 2 bar and below 6 bar pressure indicating the presence of these two mechanisms in the functionalized ionic liquids. Enhanced carbon dioxide absorption observed for functionalized ionic liquids at pressures below 2 bar indicates that the chemical reaction mechanism is acting in the carbon dioxide absorption. The viscosity of the ionic liquids increased with increase in the protons NH2 greater than NH greater than N—CH3. Use of N—C2H5 or N—C3H7 or N—C4H9 or N-aliphatic ring will help in further reducing the viscosity without compromising on the carbon dioxide absorption.

Example 14

Viscosity of Functionalized Ionic Liquids are provided in the Table 1.

| Compound | Viscosity (cP) | |
| --- | --- | --- |
|  | Pristine Sample | After Carbon dioxide absorption |
| Formula 14 | 1608 | 2510 |
| Formula 15 | 684 | 766 |
| Formula 16 | 4435 | 4565 |
| Formula 17 | 407 | 952 |
| Methyl amino propyl imidazolium NTf2 | 10,408 | — |
| Butyl amino propyl imidazolium NTf2 | 4396 | — |
| Methyl hyroxy propyl imidazolium NTf2 | 179 | — |
| Butyl hydroxy propyl imidazolium NTf2 | 158 | — |
| Hexadecyl methyl imidazolium NTf2 | 69 | — |

Example 15

Flame retardant (FR) application of containing amino and alcohol group functionalized imidazolium ionic liquids were tested by coating them onto cotton fabrics. For example, [3-hydroxypropyl-1-methyl imidazolium] bromide [OHp-mim]Br which was prepared using the method described in the Example 1 was coated on to cotton fabric. The flame retardant property of the coated fabric was evaluated using vertical flame testing. The fire is immediately extinguished when the flame was removed while the uncoated fabric turned into ashes in 20 seconds.

Example 16, 17 and 18 are comparative examples supporting this disclosure that the amino and alcohol groups are critical for the superior FR property of the ionic liquids.

Example 16

1-But-3-enyl-3-methyl-1H-imidazolium Bromide

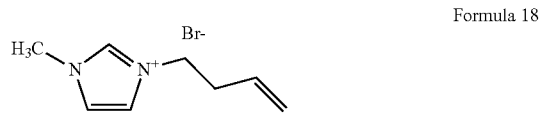

Formula 18

Methyl imidazole (2.06 g) was mixed with 4-bromobut-1-ene. (4 g) in a round bottom (RB) flask. The mixture was stirred at 40° C. for overnight. After the reaction, the product was washed with diethyl ether (5 mL 3×) and dried under high vacuum. 1-But-3-enyl-3-methyl-1H-imidazolium bromide was obtained as a clear viscous yellow colored liquid. The dried sample was analyzed with proton nuclear magnetic resonance spectroscopy (NMR). Proton NMR Data: (DMSO-D6): chemical shift [ppm]=2.72 (2H, 2'-H), 4.11 (s, 3H, NCH3), 4.48 (t, 2H, 1'-H), 5.09-5.11 (m, 1H, 4'-Ha), 5.81 (m, 1H, 3'-H), 7.62 (s, 1H, 4-H, 4-H/5-H), 7.65 (s, 1H, 4-H, 4-H/5-H), 10.19 (s, 1H, 2-H).

Example 17

1-allyl-3-methyl imidazolium bromide

Formula 19

In a typical reaction, 20 g of allyl bromide was added in drop wise to 13.4 g of methyl imidazole in a RB flask. The temperature of the reaction mixture was kept below 10 degree C. using an ice bath. After the completion of addition of allyl bromide the mixture was stirred at room temperature for 12 hours. The final product was obtained as a reddish brown liquid after washing with diethyl ether and the volatiles were removed by high vacuum evaporation at room temperature. Proton NMR Data: (DMSO-D6): chemical shift [ppm]=9.27 (s, 1H, NCHN), 7.78 (s, 2H, NCHCHN), 6.05 (m, 1H, NCH2CH@CH2), 5.32 (dd, 1H, NCH2CH@CHHtrans), 5.29 (dd, 1H, NCH2CHCHcis), 4.90 (d, 3JHH=5.8 Hz, 2H, NCH2CH@CH2), 3.84 (s, 3H, NCH3)

Example 18

Vertical Flame Testing

50 Nylon 50 Cotton Universal ripstop fabric class 6 MIL-DTL-44436B pure finish (NYCO) fabric samples were coated with aqueous solutions of 1-But-3-enyl-3-methyl-1H-imidazolium bromide and 1-allyl-3-methyl imidazolium bromide and cured at 70 degree C. for 10 minutes. Vertical flame testing data for ionic liquids based on methyl imidazolium bromide containing Carbon-Carbon double bonds are provided in Table 2. None of these ionic liquids with terminal double bond performed well under vertical flame testing. The after flame times were very high with low char yield (less than 20 percent) as provided in Table 2.

TABLE 2

Vertical flame testing data of allyl and butenyl methyl-imidazolium bromide ionic liquids

| Coating Composition in water | Avg. Weight Increase of fabric | Avg. Char Length (in) | Avg. After Flame Time (s) | Char Yield |
|---|---|---|---|---|
| 50% Allyl-methyl-imidazolium | 34.6% | N/A | 43.5 | 13.5% |
| 20% 1-Allyl-3-imidazolium/30% AMPS/5% MBAm/1% APS | 45.8% | N/A | 42.5 | 5.9% |
| 50% Allyl-methyl-imidazolium/12.5% Urea | 40.7% | N/A | 43 | 19.9% |

Example 19

This is a comparative example. Flame resistance of two ionic liquids tetrabutyl phosphonium diethyl phosphate (TPEP) and Ethyl methyl imidazolium diethyl phosphate (EIP) coated 419W cotton fabrics were measured according to standard test method ASTM 6413-08. The specimens with dimensions 3"×12" were used in this test. The specimen was maintained in a static, draft-free, vertical position. The test specimen was exposed to a flame height of 1½ inch (38 mm) for 12 seconds. After the 12-second period, the after-flame and after-glow times were determined. The char length was measured after cooling the sample. The ionic liquid coated fabrics were charred and stopped the flame propagation immediately after the removal of the flame. Vertical flame testing of TPEP and EIP based FR formulations are provided in Table 3.

TABLE 3

Vertical flame testing of commercial ionic liquids TPEP and EIP

| Coating Solution | Fabric type | Avg. Weight Increase | Avg. After Flame Time (s) | Avg. Char Yield |
|---|---|---|---|---|
| % TREP/13.6% Al(NO$_3$)$_3$ (1) | Cotton | 29.7% | 4.3 | 26.7 |
| 0% TREP/10% EIP (2) | Cotton | 28.1% | 1.5 | 41.4 |
| 0% TPEP (3) | Cotton | 22.5% | 6 | 10.5 |
| 25% EIP (4) | Cotton | 28.3% | 3.5 | 15.5 |
| 25% TREP/6.7% Urea (NYCO) | NYCO | 24.3% | 38.7 | 41.1 |

Example 20

The ionic liquid (TPEP and EIP) coated fabrics formed char during flame testing. But they also exhibited higher char length. In order to improve the flame retardant property, the TPEP-coated cotton fabric was coated with a layer of AMPS (30%) monomer and MBAm (3%) cross linker. Then the fabric was air dried for 4 days before the vertical flame testing. Cotton fabric coated with TPEP/AMPS-MBAm was subjected to vertical flame testing. The coated fabric exhibited a less vigorous flame than the uncoated control fabric. After-flame time and char length was also significantly reduced and no afterglow was observed. The vertical flame test data were provided in Table 20.

TABLE 4

Vertical flame testing of AMPS coated cotton fabrics

| Coating Solution | Avg. Weight Increase | Avg. Char Length (in) | Avg. Char Yield (%) |
|---|---|---|---|
| 20% AMPS/3% MBAm/1% APS | 15.8% | — | 38% |
| 20% AMPS/6% MBAm/1% APS | 18.4% | 9.3 | 63.9% |
| 20% AMPS/9% MBAm/1% APS | 20.6% | 10.1 | 57.6% |
| 30% AMPS/3% MBAm/1% APS | 25.1% | 9.1 | 67.6% |
| 30% AMPS/6% MBAm/1% APS | 26.6% | 5.9 | 90.5% |
| 30% AMPS/9% MBAm/1% APS | 30% | 7.1 | 83.9% |

Example 21

TABLE 5

Vertical flame testing of AMPS/TPEP coated cotton fabrics

| Coating Solution | Avg. Weight Increase | Avg. Char Length (cm) | Avg. Char Yield |
|---|---|---|---|
| 20% AMPS/4% MBAm/20% TPEP/1% APS | 43.3% | 24 | 87.7% |
| Alternating layers: 20% TPEP and 30% AMPS/6% MBAm/1% APS, 2 layers each | 48.6% | 23.4 | 88.1% |
| Alternating layers: 20% TPEP and 20% AMPS/4% MBAm/1% APS, 2 layers each | 51.4% | 24.5 | 82.2% |
| Alternating layers: 45% TPEP and 30% AMPS/6% MBAm/1% APS, 2 layers each | 47% | 20.9 | 85.5% |

Example 22

Synthesis of Tributyl Hydroxyl Propyl Phosphonium Bromide (TBOP)

Hydroxy propyl tributyl phosphonium bromide, [Bu3Pr[OH]]PBr also referred as 'TBOP-Br' or 'Formula 22" in this disclosure was synthesized by reacting tributyl phosphine, [Bu3P] with bromo propanol. 1-Bromo propanol and tributyl phosphine was mixed in a round-bottomed flask at 60-100° C. with constant stirring for 12-24 h. The reaction product was washed with diethyl ether and completely dried under vacuum at 80 degree C.

Chemical Structure of "TBOP-Br" Formula 20

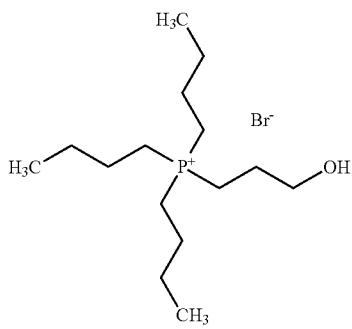

Formula 20

Example 23

Hydroxypropyl phosphonium bromide (Formula 20) prepared using the method described in the example 22 was dissolved in hydrogen bromide and heated under reflux for five hours to obtain the bromopropyl phosphonium salt represented by the chemical of the formula 21.

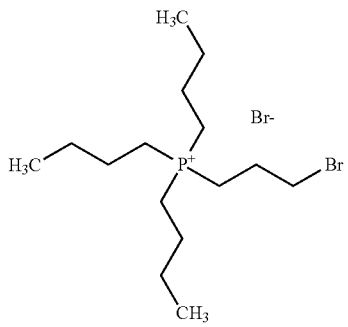

Formula 21

Example 24

Bromopropyl tributyl phosphonium salt (Formula 21) was reacted with a variety of amino alcohols to form the corresponding bromide salts. For example, Bromopropyl tributyl phosphonium bromide was reacted with N-methyl ethanolamine in the presence of potassium carbonate as provided in the reaction scheme below:

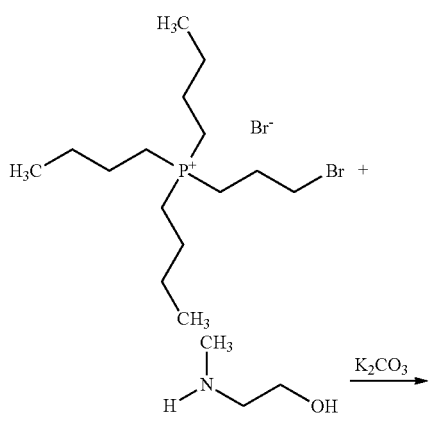

Formula 22

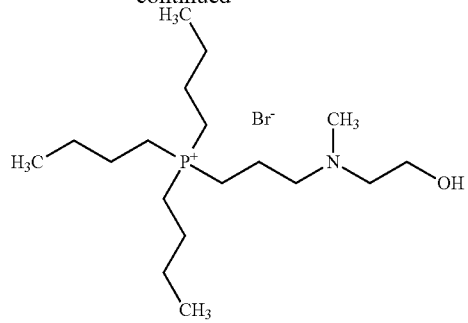

-continued

In a typical reaction, 0.02 mol of bromopropyl tributyl phosphonium bromide, 0.02 mol of N-methyl ethanolamine and 0.04 mol of potassium carbonate were mixed in 100 mL of acetonitrile and heated at 65 degree C. for 12 hours. After the reaction the product was filtered off and washed with acetonitrile. The filtrate was rotoevaporated to remove the solvent. Then extracted with tetrahydrofuran (THF) in which N-methyl amino ethanol is soluble. Then the sample is dried under high vacuum.

Example 25

Termogravimetric Analysis of Formula 20 (TBOP-Br) Coated NYCO Fabric

Figure 17:
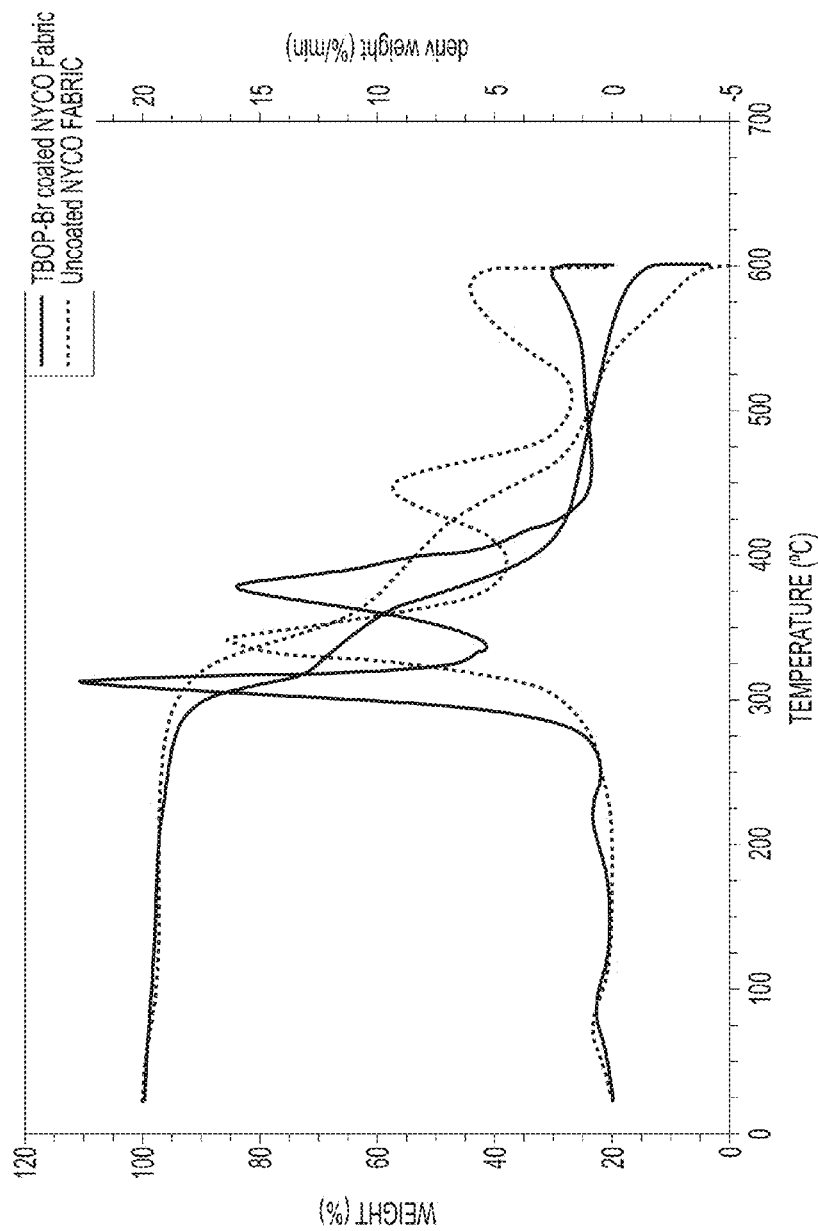
FIG. 17. Overlay plot of TGA data of uncoated-NYCO fabric and TBOP coated NYCO fabric FIG. 18. Proton NMR spectrum of TBAP-DBP ionic liquid FIG. 19. P-31 NMR spectrum of TBAP-DBP ionic liquid FIG. 20. Vertical flame test data of TBAP-DBP based flame retardants as a function of urea addition FIG. 21. Comparison of flame retardant property as function of anions FIG. 22. Pictures of the flammability of dimethylcarbonate (DMC) and fire-quenching effect of the phosphonium ionic liquid, TBAP-Br.

Thermogravimetric analysis (TGA) can be helpful in deducing the decomposition mechanism of flame retardant coated fabric. Therefore, the thermal degradation behaviors of uncoated NYCO (control) and TBOP-Br/Urea coated NYCO fabrics were analyzed using TGA. TGA curves were obtained using a TA Instruments TGA2950. The purge atmosphere was air at 100 ml/min. The temperature program was a ramp at 20 degree C. per minute to 600 degree C. with a 15 minute hold. The sample was in a disposable aluminum liner in a platinum pan for weight with the precision weight set provided by TA Instruments. High thermal stability of TBOP-Br ionic liquid was clearly demonstrated by the TGA curve provided in FIG. 17. The initial decomposition temperature of TBOP is about 290 degree C. Thermal decomposition of NYCO fabric in air occurs in two stages according to the TGA data provided in FIG. 17. The first stage decomposing temperature of uncoated-NYCO fabric is 342 degree C. corresponds to the decomposition of cotton in the NYCO fabric. This decomposition temperature is shifted to 311 degree C. by the phosphonium catalyzed decomposition of cotton. This behavior is similar to the behavior of Tetrakis(hydroxymethyl) phosphonium chloride (THPC) flame retardant material. But the initial decomposition temperature of THPC is around 184 degree C. compared to 311 degree C. for TBOP-Br indicating the relatively higher thermal stability of TBOP-Br. The second stage weight loss is centered around 446 degree C. is due to the decomposition of Nylon material in the NYCO fabric. This decomposition temperature is also decreased in the TBOP/Urea coated NYCO fabric. The residue from sample TBOP-Br/Urea coated fabric was a rigid black solid with the original sample form and fabric weave patterns visible. The residue from uncoated NYCO fabric was a fluffy white solid. These observations clearly demonstrated the efficient char formation in the case of phosphonium ionic liquid coated samples supporting the observations made during the vertical flame testing.

Example 26

Antielectrostatic Property of Ionic Liquids

Ionic liquids consist of charged species with high ionic conductivity. The static charge accumulated on the fabric surface can be rapidly dissipated by conducting ions. Antistatic property of the TBOP-Br/Urea treated fabrics were tested using the Federal Test Method Standard 191A Method 5931 'Determination of electrostatic decay of fabrics'. According to this method the amount of time it takes for static to dissipate from a fabric strip was measured. The 3"×5" test samples were pre-conditioned at 20% relative humidity at 24° C. 5000 V was applied to the test fabric for a period of 20 seconds. The voltage behavior of the test sample as a function of decay time was recorded. The time for the charge to decay from the maximum voltage level to 50% of the maximum voltage attained was measured from the voltage decay plot. The decay time for the uncoated and TBOP/Urea coated fabrics were provided in Table 6.

TABLE 6

Antistatic property of TROP-Br/Urea coated NYCO samples

| SampleType | Electrical Charge Decay Time (s) | |
|---|---|---|
| | Uncoated NYCO | TBOP coated NYCO |
| Warp | 7.8 | 1.2 |
| Fill | 9.0 | 1.2 |

The antistatic property of the ionic liquid coated fabric was clearly demonstrated in the data provided in the Table 6. The electric charge applied on to the TBOP-Br/Urea coated fabric was rapidly removed compared to uncoated NYCO fabric.

Example 27

TABLE 7

Vertical flame testing data of TROP-Br ionic liquid

| Coating Composition on NYCO fabric | Avg. Weight Increase | Avg. Char Length (inch) | Avg. After Flame Time (seconds) |
|---|---|---|---|
| 50% TBOP-Br | 35.1% | — | 36.3 |
| 50% TBOP-Br/ 4.5% Urea | 38.2% | 4.3 | 2.5 |

Example 28

Formula 23—Tributyl Amino Propyl Phosphonium Bromide (TBAP-Br)

Amino propyl tributyl phosphonium bromide, [Bu3Pr[NH2]]PBr also referred as 'TBAP-Br' or 'Formula 23" was synthesized by reacting tributyl phosphine, [Bu3P] with 3-bromopropylamine hydrobromide. 3-bromopropylamine hydrobromide and 1-methyl imidazole was mixed with acetonitrile in a round-bottomed flask at 80° C. with constant stirring for 12-24 h. The reaction product was washed with hexane to remove unreacted reactants and completely dried under vacuum at 80 degree C.

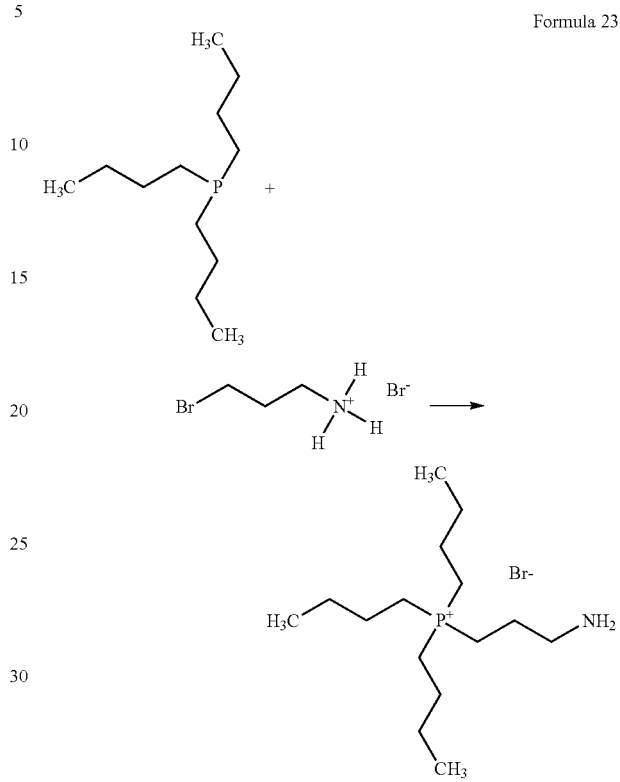

Formula 23

Proton NMR (CDCl3) Data: chemical shift 0.93 (t, 9H; CH3), 1.47-1.63 (m, 12H; CH-2), 2.25-2.39 (M, 8H; PCH2), 2.9 (m, 2H, CH2NH2), 3.35 ppm (t, 2H, CH2NH2); P-31 NMR DATA: chemical shift=34 ppm corresponding to phosphonium salt

Example 29

Vertical Flame Testing of TBAP-Br

TBAP-Br was coated onto NYCO fabric with and without mixing with urea. The combination of TBAP-Br and urea produced excellent results, with an average char length of 4.37 inches, and an average char yield of 93.1%. Pure TBAP-Br produced good data as well, with averages of 5.16 inch char length and 91.9% char yield. The vertical flame test data are provided in Table 8. Phosphorus-Nitrogen synergism It is a well-known fact that there exists a phosphorus-nitrogen (P—N) synergistic action in the flame retardancy of cellulosic fibers. Addition of nitrogen containing compounds, such as urea, cyanamides, dicyandiamide, guanidine salts, and melamine compounds to phosphorus compounds increase their flame retardancy, even though they themselves do not exhibit FR property. In TBAP both P and N present in the same molecule. In this way TBAP is analogous to [TBOP+Urea] formulation.

TABLE 8

Vertical flame test data of TBAP and TBAP/Urea coated NYCO fabrics

| Coating Compostion in water | Avg. Weight Increase | Avg. Char Length (in) | Avg. After Flame Time (s) | Char Yield |
|---|---|---|---|---|
| 50% TRAP-Br Formula 23 | 39.3% | 5.16 | 2.0 | 91.9% |
| 50% TRAP-Br/7.0% Urea on NYCO | 38.2% | 4.37 | 2.0 | 93.1% |

Example 30

Bromide Ion-Exchange of TBAP-Br

Tributyl-Propyl Amino Phosphonium Dibutylphosphate (TBAP-DBP) Formula 24

TBAP with a dibutyl phosphate (DBP) anion was prepared by dissolving equimolar amounts of TBAP-Br and DBP in methanol, followed by the addition of an equimolar amount of potassium hydroxide. The mixture was stirred for 12 hours and the resulting in TBAP-DBP ionic liquid and a potassium bromide salt. The methanolic solution was filtered and evaporated under vacuum, to separate the TBAP-DBP ionic liquid. The ion-exchange reaction can represented as follows:

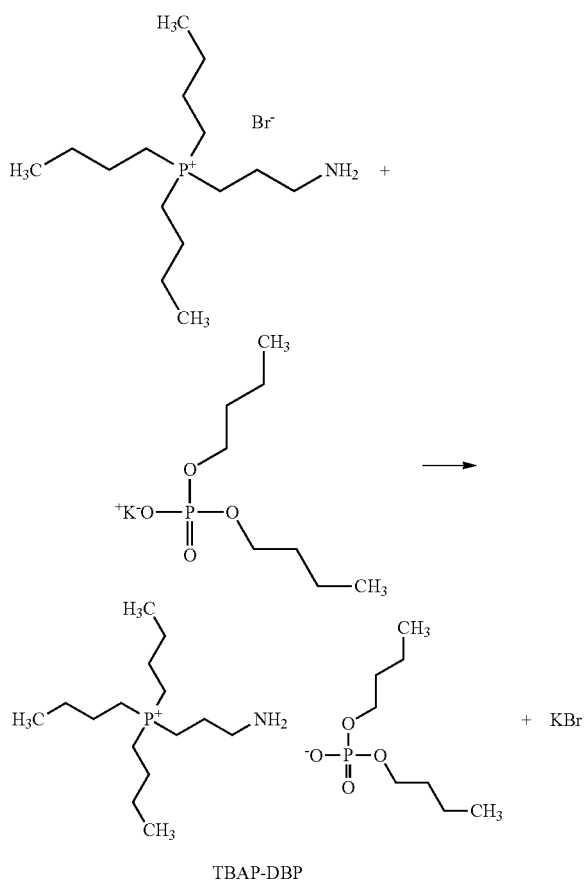

TBAP-DBP

Figure 18:
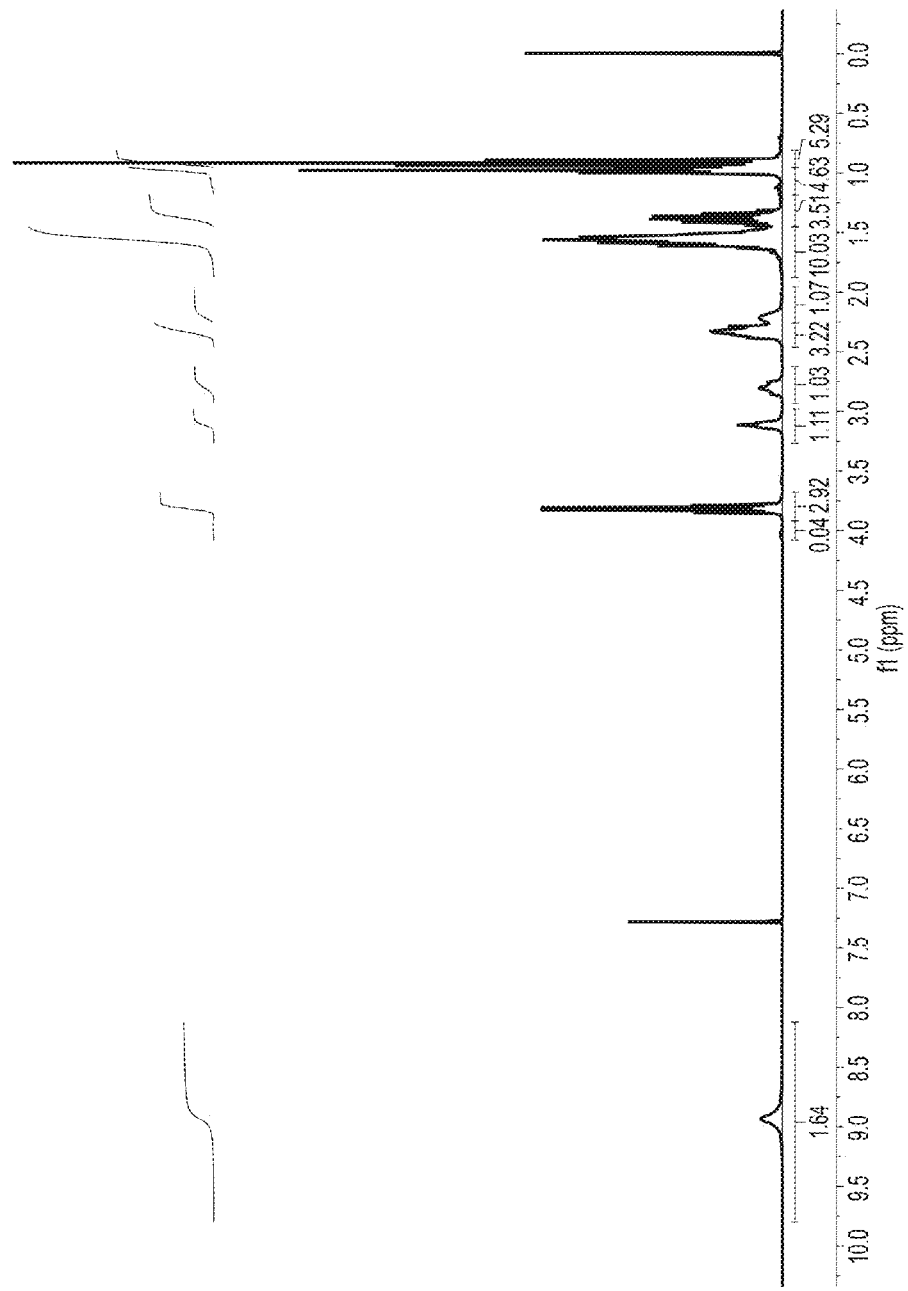
Figure 19:
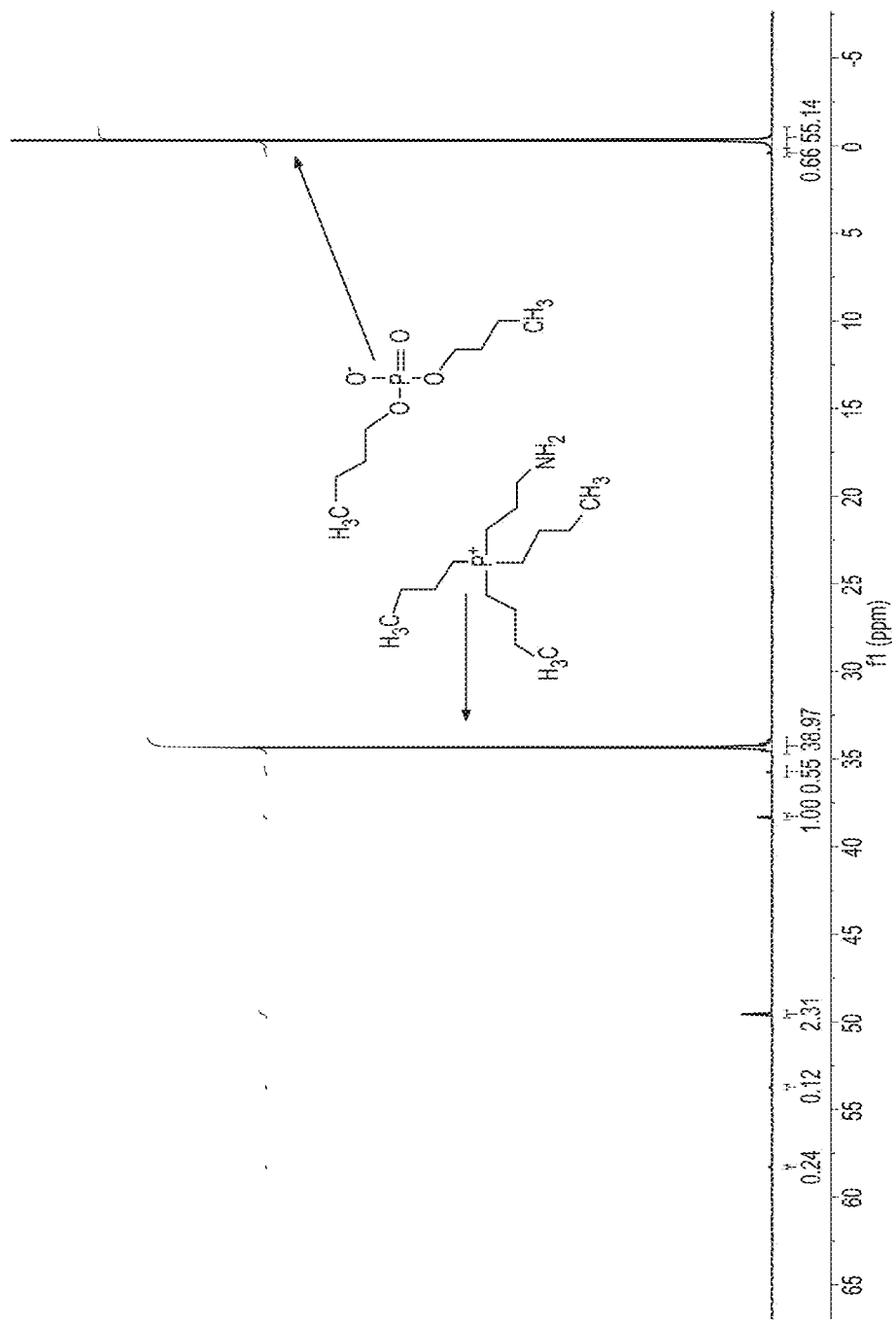

Proton NMR and C-13 NMR spectra of TBAP-DBP ionic liquid were provided in FIGS. 18 and 19 respectively.

Figure 20:
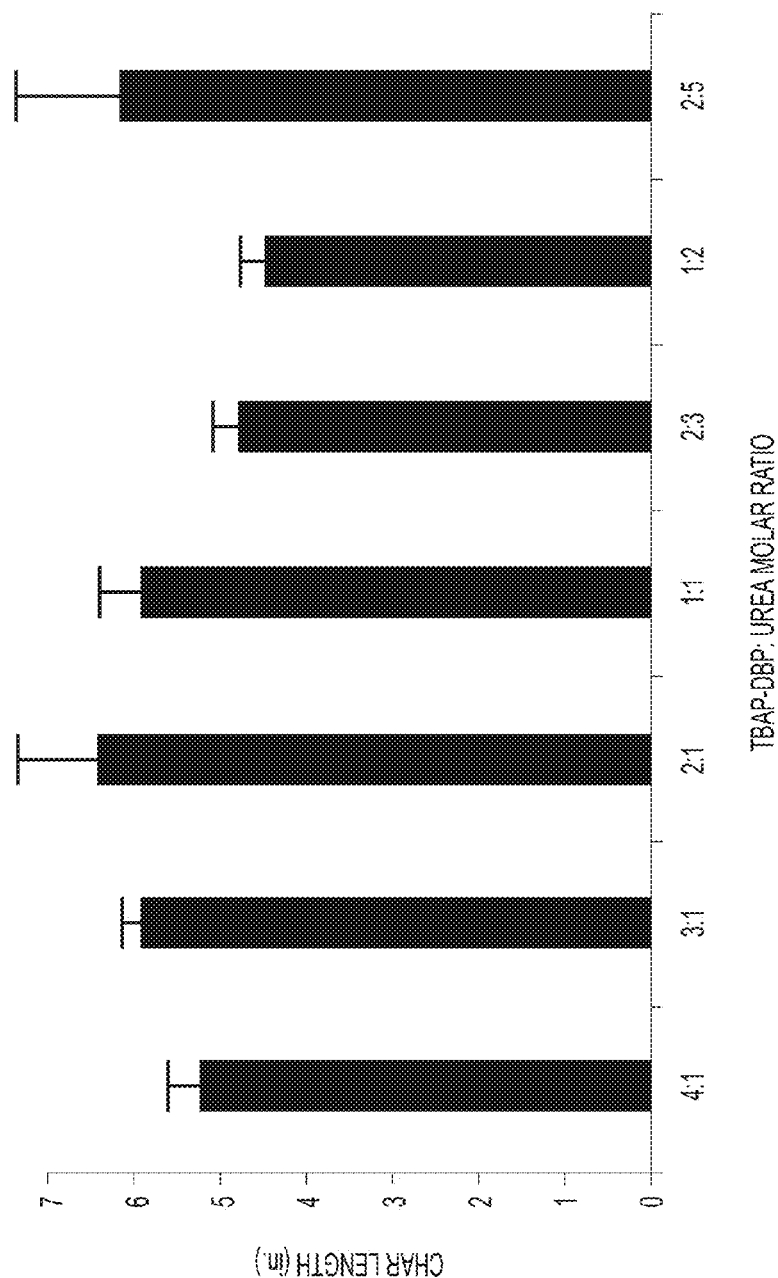

Since TBAP-DBP has two P-moieties, it was necessary to adjust the TBAP-DBP/Urea ratio in the FR coating to achieve best FR performance. The TBAP-DBP/Urea molar ratio was varied between 4:1 to 2:5 and the vertical flame test data are provided in FIG. 20 and Table 9. Lowest char length (4.1 inch) and best char yield (91%) were observed with 1:2 TBAP-DBP/Urea molar ratio. These data clearly demonstrate the action of 'Phosphorus-Nitrogen synergism' on the flame retardant property of phosphonium based chemicals with the optimum P:N ratio of 2:3.

TABLE 1

Vertical Flame Testing Data of TBAP-DBP

| Coating Composition in water | Avg. Weight Increase | Avg. After Flame Time (s) | Char Yield |
|---|---|---|---|
| 50% TBAP-DBP/1.5% Urea | 36.7% | 1.0 | 89.0% |
| 50% TBAP-DBP/2.1% Urea | 37.3% | 2.0 | 85.6% |
| 50% TBAP-DBP/3.1% Urea | 32.3% | 2.0 | 85.0% |
| 50% TBAP-DBP/5.5% Urea | 34.7% | 2.7 | 87.8% |
| 50% TBAP-DBP/9.5% Urea | 39.9% | 0.7 | 90.6% |
| 50% TBAP-DBP/12.8% Urea | 38.0% | 1.0 | 90.6% |
| 50% TBAP-DBP/16% Urea | 36.4% | 4.7 | 83.7% |

Example 31

Tributyl-propyl Amino Phosphonium Acetate (TBAP-Acetate) Formula 25

Bromide anion was replaced with the acetate anion ($CH_3COO^-$) by dissolving equimolar amounts of TBAP-Br and potassium acetate in methanol. The exchange occurred while stirring for 24 hours, and the final product of TBAP-Acetate was isolated through vacuum drying and washing with acetonitrile. Potassium salts provide an efficient means of bromide ion exchange as the KBr product is easily separated from the product by filtration due to its insolubility in acetonitrile.

The vertical flame test data of acetate anion is compared with other anions of TBAP in FIG. 21. All the TBAP-based ionic liquids tested exhibited excellent flame retardant properties with the average char length <4.5 in. indicating that the major influence on flame retardant property is due to TBAP cation.

Among various TBAP-based ionic liquids tested, TBAP-Acetate exhibited lowest char length of 4.1 in. This could be attributed to lower molecular weight of acetate anion and rationalized as follows: With the equivalent coating weight increase (~35%) in all the TBAP ionic liquids, the concentration of TBAP cation is maximum in the case of TBAP-acetate. Because the TBAP cation is the major contributor to the flame retardant property, TBAP-Acetate exhibits the best FR property among the TBAP ionic liquids tested.

Example 32

Figure 22:
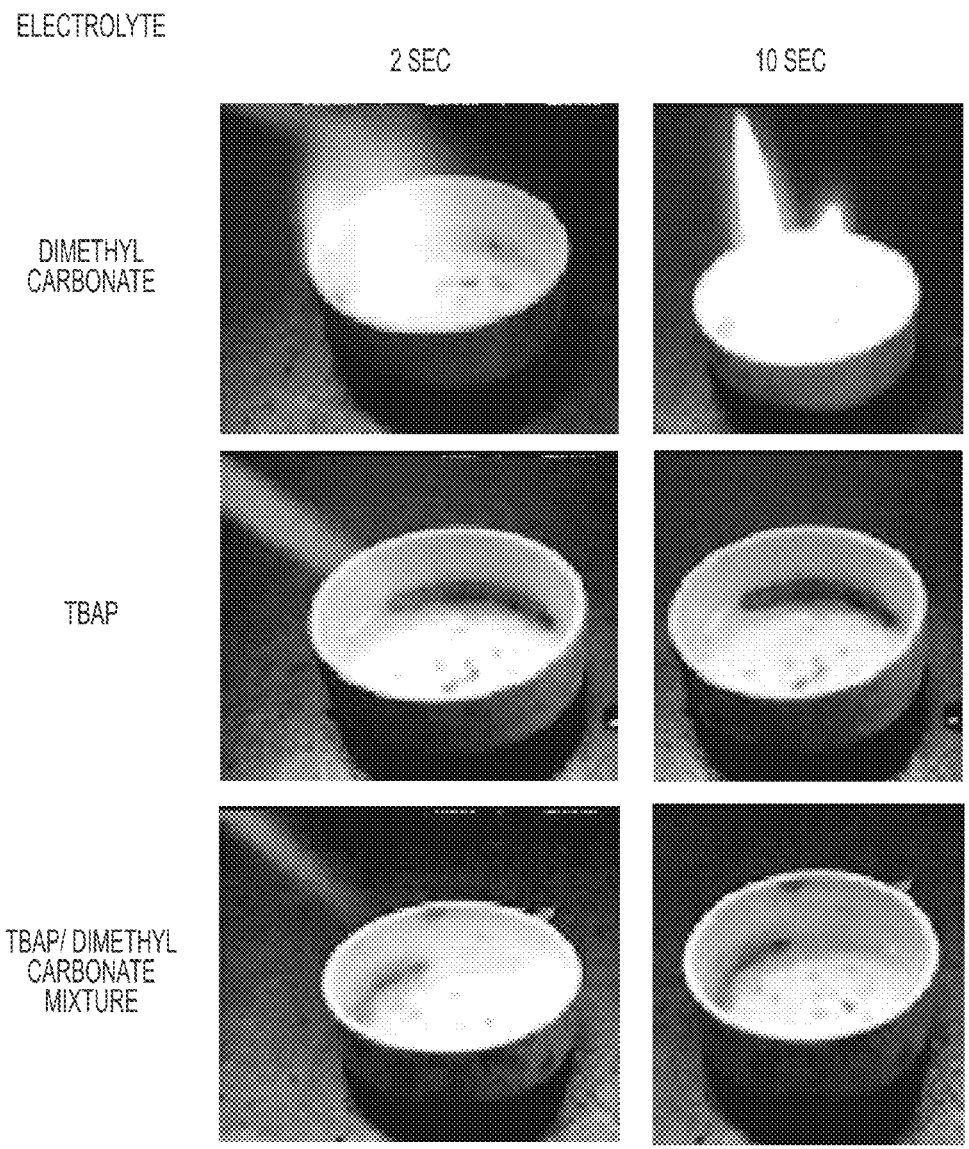

The flammability of organic carbonate electrolyte (DMC) and fire quenching action of amino-functionalized phosphonium ionic liquid was demonstrated in FIG. 22. When DMC was flashed with a propane gas burner it immediately catches fire and is completely consumed by the flame. In contrast, TBAP-Br as well as TBAP-Br/DMC mixtures when torched with propane gas burners quenches the fire in less than 10 seconds demonstrating the flame retardant property of the phosphonium based ionic liquids. The flame retardant phosphonium ionic liquids can be applied as electrolytes or electrolyte additives in lithium ion batteries.

Example 33

Melamine-Formaldehyde Condensate resins including but limited to Aerotex resins M3 were mixed with cross-linkers including but not limited to Aerotex 3730 tested with TBAP/TBOP material for FR properties and coating durability. A typical preparation of durable FR Coated NYCO fabric involved the following steps. FR coating solutions were prepared by mixing 30 g of TBAP-Br, 4.5 grams of Aerotex M3 and 9 grams of Aerotex 3730 in 60 mL of water. The solution was stirred until clear, and then 0.6 g ammonium chloride was added. Fabric samples were placed in cans along with the coating solution and agitated in a launderometer for 45 minutes at room temperature. The wetted samples were then run through a padder at 5 psi and cured at 150° C. for two minutes in an oven. Two of each set of samples were flame tested unwashed to determine initial FR performance, and subsequent samples were washed with cold water and then flame tested to evaluate durability of the coating. Vertical flame testing data as a function of binder and cross-linker concentration keeping the TBAP-Br concentration constant is provided in Table 10.

TABLE 14

Vertical flame testing as function of Melamine-Formaldehyde Condensate and crosslinking agent concentration

| Melamine-Formaldehyde Condensate | Cross-linker | Unwashed Char Length (in.) | Washed Char Length (in.) |
|---|---|---|---|
| 7.5 | 15 | 7.75 | 9 |
| 8 | 12 | 7 | 8.5 |
| 8.5 | 17 | 5.75 | 8 |
| 8 | 10.7 | 7.25 | 8.5 |

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. An ionic liquid represented by the structure of the following Formula 1:

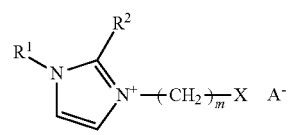

Formula 1 wherein
(a) $R^1$ and $R^2$ are each independently H, or a $C_1$ to $C_{12}$ straight-chain alkyl group or branched alkyl group or aryl group,
(b) m is an integer 1 to 6,
(c) X is $-N(R^3)-(CH_2)_q-OH$, wherein $R^3$ is H or $C_1$ to $C_6$ straight-chain or branched alkyl group and q is an integer from 2 to 4, and
(d) $A^-$ is an anion selected from the group consisting of $[BF_4]^-$, $[PF_6]^-$, $[CH_3CO_2]^-$, $[HSO_4]^-$, $[CF_3SO_3]^-$, $[(CF_3SO_2)_2N]^-$, $[(CF_3SO_2)_3C]^-$, $[SO_4]^{2-}$, $Cl^-$, $Br^-$, $I^-$, $[N(CN)_2]^-$, $[(PO_4)(C_4H_9)_2]^-$, $[(PO_4)(C_2H_5)_2]^-$, $[(PO_4)(C_6H_5)_2]^-$, $[CH_3CH_2OSO_3]^-$, $[CH_3OCO_2]^-$ and amino acid.

2. A fire retardant coating for textile fabrics comprising the ionic liquid of claim 1.

3. A solvent for carbon dioxide capture comprising the ionic liquid of claim 1.

4. An electrolyte in a lithium ion battery comprising the ionic liquid of claim 1.

5. A flame retardant additive to an electrolyte in a lithium ion battery comprising the ionic liquid of claim 1.

6. An electrolyte in a metal air battery comprising the ionic liquid of claim 1.

7. A flame retardant additive to an electrolyte in a metal air battery comprising the ionic liquid of claim 1.

8. An antistatic coating comprising the ionic liquid of claim 1.

* * * * *